(12) United States Patent
Gray

(10) Patent No.: US 12,257,322 B2
(45) Date of Patent: Mar. 25, 2025

(54) OPTIMIZED CLN1 GENES AND EXPRESSION CASSETTES AND THEIR USE

(71) Applicant: The University of North Carolina at Chapel Hill, Chapel Hill, NC (US)

(72) Inventor: Steven Gray, Southlake, TX (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 6 days.

(21) Appl. No.: 18/052,082

(22) Filed: Nov. 2, 2022

(65) Prior Publication Data

US 2023/0372544 A1 Nov. 23, 2023

Related U.S. Application Data

(62) Division of application No. 16/305,337, filed as application No. PCT/US2017/037118 on Jun. 13, 2017, now Pat. No. 11,504,435.

(60) Provisional application No. 62/349,411, filed on Jun. 13, 2016.

(51) Int. Cl.
*A61K 48/00* (2006.01)
*C12N 15/86* (2006.01)

(52) U.S. Cl.
CPC .......... *A61K 48/0066* (2013.01); *C12N 15/86* (2013.01); *C12N 2750/14143* (2013.01); *C12N 2750/14145* (2013.01); *C12N 2830/002* (2013.01)

(58) Field of Classification Search
CPC ............ A61K 48/0066; A61K 31/7088; A61K 48/00; C12N 15/86; C12N 2750/14143; C12N 2750/14145; C12N 2830/002; C12N 9/16; C12N 15/8509; C12N 2750/14141; C12N 2800/22; C12N 15/52; A01K 2217/075; A01K 2227/105; A01K 2267/0356; A61P 25/00; A61P 25/28; C12Y 301/02022
See application file for complete search history.

(56) References Cited

U.S. PATENT DOCUMENTS

| 6,582,692 | B1 | 6/2003 | Podsakoff et al. |
| 7,442,372 | B2 | 10/2008 | Kakkis |
| 7,906,111 | B2 | 3/2011 | Wilson et al. |
| 8,242,086 | B2 | 8/2012 | Boustany |
| 9,926,574 | B2 | 3/2018 | Barkats |
| 10,208,318 | B2 | 2/2019 | Barkats |
| 10,301,648 | B2 | 5/2019 | Vandenberghe et al. |
| 2003/0083299 | A1 | 5/2003 | Ferguson |
| 2015/0313863 | A1 | 11/2015 | Kalipada |

FOREIGN PATENT DOCUMENTS

| AU | 2014337783 A1 | 5/2016 |
| EP | 1620133 A1 | 2/2006 |
| RU | 2330861 C2 | 8/2008 |
| WO | 2001092551 A1 | 12/2001 |

OTHER PUBLICATIONS

"Decision to Grant corresponding to Russian Application No. 2018145010 issued Nov. 22, 2021".
"Examination Report corresponding to European Application No. 17813890.5 dated Dec. 10, 2020".
"Examination Report corresponding to European Application No. 17813890.5 dated Mar. 11, 2022".
"Extended European Search Report corresponding to European Application No. 17813890.5 dated Jan. 7, 2020".
"Gray, "Gene therapy for INCL", Workshop, Batten Disease: 2016 Update of Translational Research for Management of INCL/LINCL, Bethesda, MD, Mar. 30-31, 2016".
"International Preliminary Report on Patentability corresponding to International Application No. PCT/US2017/037118 mailed Dec. 27, 2018".
"International Search Report and Written Opinion corresponding to International Application No. PCT/US2017/037118 mailed Aug. 31, 2017".
"Office Action corresponding to Japanese Application No. 2018-564943 mailed Jun. 28, 2021".
"Office Action corresponding to Australian Application No. 2017284198 dated Sep. 29, 2022".
"Office Action corresponding to Brazilian Application No. 112018075692-0 issued Oct. 11, 2022".
"Office Action corresponding to Chinese Application No. 201 7800367811 issued Apr. 6, 2021".
"Office Action corresponding to Chinese Application No. 201780036781.1 issued Jan. 5, 2022".
"Office Action corresponding to Israeli Application No. 263,009 issued Oct. 21, 2021".
"Office Action corresponding to Japanese Application No. 2018-564943 mailed Mar. 3, 2022".
"Office Action corresponding to Korean Application No. 10-2018-7035890 issued Jul. 20, 2022".
"Office Action corresponding to Mexican Application No. MX/a/2018/015461 issued Jul. 1, 2022".
"Office Action corresponding to Russian Application No. 2018145010 issued Dec. 23, 2020".
Asanov, A. Yu, et al., "Fundamentals of genetics and hereditary developmental disorders in children", Moscow: Publishing Center "Academy", 2003, 214 pages.

(Continued)

*Primary Examiner* — Jeremy C Flinders
*Assistant Examiner* — Alexander W Nicol
(74) *Attorney, Agent, or Firm* — Myers Bigel, P.A.

(57) ABSTRACT

This invention relates to polynucleotides comprising a nucleotide sequence encoding a PPT1 polypeptide or a fragment thereof, vectors (viral or non-viral vectors) comprising the same, and methods of using the same for delivery of the open reading frame to a cell or a subject and to treat infantile neuronal lipofuscinosis (infantile Batten disease). The polynucleotides comprise an optimized CLN1 open reading frame.

22 Claims, 16 Drawing Sheets

Specification includes a Sequence Listing.

(56) References Cited

OTHER PUBLICATIONS

Bosch , et al., ""Long-Term and Significant Correction of Brain Lesions in Adult Mucopolysaccharidosis Type VII Mice Using Recombinant AAV Vectors", Molecular Therapy 1(1):63-70 (2000)".
Brown, Harrison C, et al., "Tissue Directed Transgene Engineering for AAV and Lentivector Gene Therapy Approaches", Molecular Therapy 24(Suppl. 1):S287 Abstract No. 728 (May 2016).
Bulatnikova, M A., et al., "Clinical observation of 1st type neuronal lipofuscinosis (Santavuori-Haltia syndrome)", Kliniko-laboratornyij konsilium, 2012, No. 2(42), pp. 48-52 (see the abstract).
Büning , et al., ""Recent developments in adeno-associated virus vector technology", J Gene Med 10:717-733 (2008)".
Dennis, M. B., "Welfare issues of genetically modified animals", ILAR Journal, 2002, vol. 43, Issue 2, pp. 100-109.
Griffey , et al., ""Adeno-associated virus 2-mediated gene therapy decreases autofluorescent storage material and increases brain mass in a murine model of infantile neuronal ceroid lipofuscinosis", Neurobiology of Disease 16:360-369 (2004)".
Griffey , et al., ""CNS-Directed AAV2-Mediated Gene Therapy Ameliorates Functional Deficits in a Murine Model of Infantile Neuronal Ceroid Lipofuscinosis", Molecular Therapy 13(3):538-547 (2006)".
Kollmann , et al., ""Cell biology and function of neuronal ceroid lipofuscinosis-related proteins", Biochimica et Biophysica Acta 1832:1866-1881 (2013)".
Mauro, Vincent P., et al., "A critical analysis of codon optimization in human therapeutics", Trends in Molecular Medicine, 20(11), 2014, 604-613.
Michelfelder , et al., ""Peptide Ligands Incorporated into the Threefold Spike Capsid Domain to Re-Direct Gene Transduction of AAV8 and AAV9 In Vivo", PLOS ONE 6(8):e23101 (2011) 11 pages".
Parret, Annabel Ha, et al., "Critical Reflections on synthetic gene design for recombinant protein expression", Current Opinion in Structural Biology 38:155-162 (2016).
Rozenberg, Alejandra J., et al., "362. Translatable Gene Therapy for Infantile Neuronal Lipofuscinosis", Molecular Therapy 24 (May 2016):S145.
Sen , et al., ""Targeted Modifications in Adeno-Associated Virus Serotype 8 Capsid Improves Its Hepatic Gene Transfer Efficiency In Vivo", Human Gene Therapy Methods 24:104-116 (2013)".
Vance, Melisa , et al., "AAV gene therapy for MPS1-associated corneal blindness", Scientific Reports, 6(1) (Feb. 22, 2016), 2016, 1-10.
Xiao, Weidong , et al., "Gene therapy vectors based on adeno-associated virus type 1", Journal of Virology, 73(5), 1999, 3994-4003.
Zhou, H. , et al., "Developing tTA transgenic rats for inducible and reversible gene expression", International Journal of Biological Sciences, 2009, vol. 5, Issue 2, pp. 171-181.
"Office Action corresponding to Korean Application No. 10-2018-7035890 issued Mar. 29, 2023".
"Examination Report corresponding to European Application No. 17813890.5 dated Jul. 16, 2024".
Gessler, Dominic J, et al., "Redirecting N-acetylaspartate metabolism in the central nervous system normalizes myelination and rescues Canavan disease", JCI Insight. 2(3):e90807 (Feb. 9, 2017) 17 pages.
"Office Action corresponding to Brazilian Application No. 112018075692-0 issued Nov. 4, 2024".

OPTIMIZED CLN1 GENES AND EXPRESSION CASSETTES AND THEIR USE

STATEMENT OF PRIORITY

This application is a divisional of and claims priority to U.S. patent application Ser. No. 16/305,337, filed Nov. 28, 2018, now allowed, which is a 35 U.S.C. § 371 national phase application of PCT/US2017/037118, filed Jun. 13, 2017, which claims the benefit of U.S. Provisional Application Ser. No. 62/349,411, filed Jun. 13, 2016, the entire contents of which are incorporated by reference herein.

STATEMENT REGARDING ELECTRONIC FILING OF A SEQUENCE LISTING

A Sequence Listing in XML format, submitted under 37 C.F.R. § 1.831-1.834, entitled 5470-788DV_ST26.xml, 12,460 bytes in size, generated on Nov. 1, 2022 and filed electronically, is provided in lieu of a paper copy. This Sequence Listing is hereby incorporated by reference into the specification for its disclosures.

FIELD OF THE INVENTION

This invention relates to polynucleotides comprising optimized CLN1 open reading frame (ORF) sequences, vectors (viral or non-viral vectors) comprising the polynucleotides, and methods of using the polynucleotides for delivery of the CLN1 ORF to a cell or a subject and methods of using the polynucleotides for treating infantile neuronal lipofuscinosis (infantile Batten disease).

BACKGROUND OF THE INVENTION

Neuronal ceroid lipofuscinosis (NCL) refers to a family of at least eight genetically different neurodegenerative disorders that result from excessive accumulation of lipopigments (lipofuscin) in the body's tissues. These lipopigments are made up of fats and proteins. The lipofuscin materials build up in neuronal cells and many organs, including the liver, spleen, myocardium, and kidneys.

The infantile form of the disease, known as infantile neuronal ceroid lipofuscinosis (INCL) or infantile Batten disease, is caused by mutations in the CLN1 gene and is an autosomal recessive disorder. Some children with mutations in CLN1 have a later onset of symptoms and slower disease progression, which resembles juvenile onset disease and is more typically associated with mutations in the CLN3 gene. The CLN1 gene, located at 1p32, encodes a lysosomal enzyme called palmitoyl protein thioesterase 1 (PPT1). A deficiency of PPT1 results in abnormal storage of proteins and lipids in neurons and other cells and impaired cellular function.

There are no effective treatments for INCL, although there have been attempts with enzyme replacement therapy (see, e.g., U.S. Pat. No. 7,442,372) and gene therapy. Administration of neural stem cells and other agents has also been tested (see, e.g., U.S. Pat. No. 8,242,086, US Publication No. 2015/0313863), but the clinical efficacy of such methods are still under study.

Therefore, there is a need for a new, effective therapy for treating disorders associated with CLN1 expression such as INCL.

SUMMARY OF THE INVENTION

The present invention is based, at least in part, on the development of optimized CLN1 genes, expression cassettes, and vectors capable of providing therapeutic levels of CLN1 expression for treating disorders associated with CLN1 expression such as INCL.

Thus, one aspect of the invention relates to a polynucleotide encoding PPT1 polypeptide or a fragment thereof, wherein the nucleotide sequence is codon-optimized for expression in a human cell. In one embodiment, the polynucleotide comprises a human CLN1 open reading frame.

A further aspect of the invention relates to an expression cassette comprising a polynucleotide encoding PPT1 polypeptide or a fragment thereof and vectors, transformed cells, and transgenic animals comprising the polynucleotide of the invention. In one embodiment, the polynucleotide comprises a human CLN1 open reading frame.

Another aspect of the invention relates to a pharmaceutical formulation comprising the polynucleotide, expression cassette, vector, and/or transformed cell of the invention in a pharmaceutically acceptable carrier.

Another aspect of the invention relates to a method of expressing a polynucleotide encoding PPT1 or a fragment thereof in a cell, comprising contacting the cell with the polynucleotide, expression cassette, and/or vector of the invention, thereby expressing the polynucleotide or its fragment in the cell. In one embodiment, the polynucleotide comprises a CLN1 open reading frame. In another embodiment, the CLN1 open reading frame is a human CLN1 open reading frame. In another embodiment, the CLN1 open reading frame is codon-optimized for expression in human cells.

A further aspect of the invention relates to a method of expressing a PPT1 polypeptide or a fragment thereof in a subject, comprising delivering to the subject the polynucleotide, expression cassette, vector, and/or transformed cell of the invention, thereby expressing the PPT1 polypeptide or fragment thereof in the subject. In one embodiment, the polynucleotide comprises a CLN1 open reading frame. In another embodiment, the CLN1 open reading frame is a human CLN1 open reading frame.

An additional aspect of the invention relates to a method of treating a disorder associated with aberrant expression of a CLN1 gene or a PPT1 polypeptide or aberrant activity of a CLN1 gene product in a subject in need thereof, comprising delivering to the subject a therapeutically effective amount of the polynucleotide, expression cassette, vector, and/or transformed cell of the invention, thereby treating the disorder associated with aberrant expression of the CLN1 gene in the subject or PPT1 polypeptide.

Another aspect of the invention relates to a polynucleotide, an expression cassette, a vector, and/or a transformed cell of the invention for use in a method of treating a disorder associated with aberrant expression of a CLN1 gene in a subject in need thereof.

These and other aspects of the invention are set forth in more detail in the description of the invention below.

DETAILED DESCRIPTION OF THE INVENTION

Figure 1:
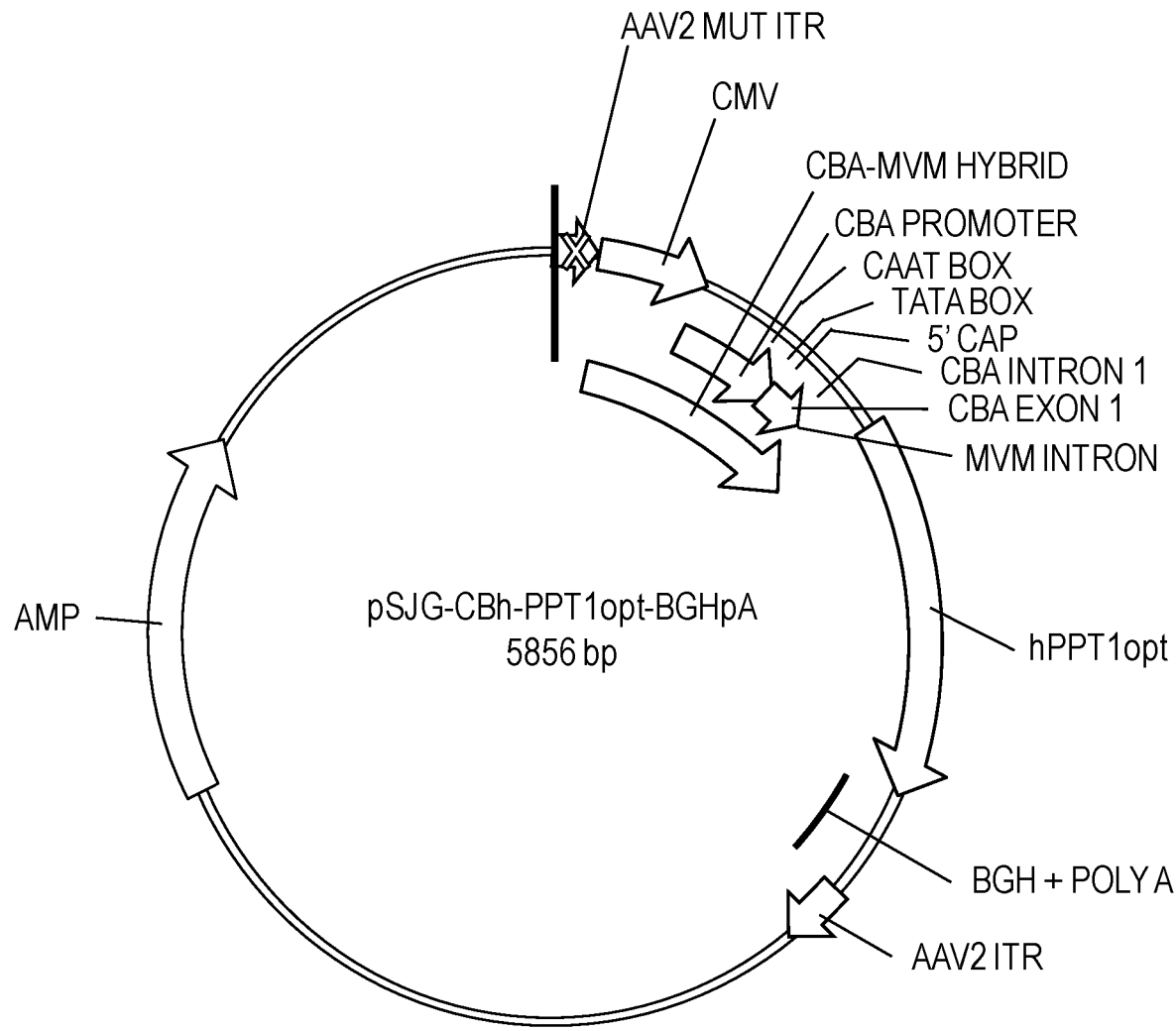
FIG. 1 shows a map of a CLN1 expression cassette.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 C.F.R. § 1.822 and established usage.

Except as otherwise indicated, standard methods known to those skilled in the art may be used for production of recombinant and synthetic polypeptides, antibodies or antigen-binding fragments thereof, manipulation of nucleic acid sequences, production of transformed cells, the construction of rAAV constructs, modified capsid proteins, packaging vectors expressing the AAV rep and/or cap sequences, and transiently and stably transfected packaging cells. Such techniques are known to those skilled in the art. See, e.g., SAMBROOK et al., MOLECULAR CLONING: A LABORATORY MANUAL 2nd Ed. (Cold Spring Harbor, N Y, 1989); F. M. AUSUBEL et al. CURRENT PROTOCOLS IN MOLECULAR BIOLOGY (Green Publishing Associates, Inc. and John Wiley & Sons, Inc., New York).

All publications, patent applications, patents, nucleotide sequences, amino acid sequences and other references mentioned herein are incorporated by reference in their entirety.

Definitions

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

Moreover, the present invention also contemplates that in some embodiments of the invention, any feature or combination of features set forth herein can be excluded or omitted.

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

As used herein, the transitional phrase "consisting essentially of" is to be interpreted as encompassing the recited materials or steps and those that do not materially affect the basic and novel characteristic(s) of the claimed invention. Thus, the term "consisting essentially of" as used herein should not be interpreted as equivalent to "comprising."

The term "consists essentially of" (and grammatical variants), as applied to a polynucleotide or polypeptide sequence of this invention, means a polynucleotide or polypeptide that consists of both the recited sequence (e.g., SEQ ID NO) and a total of ten or less (e.g., 1, 2, 3, 4, 5, 6, 7, 8, 9, or 10) additional nucleotides or amino acids on the 5' and/or 3' or N-terminal and/or C-terminal ends of the recited sequence or between the two ends (e.g., between domains) such that the function of the polynucleotide or polypeptide is not materially altered. The total of ten or less additional nucleotides or amino acids includes the total number of additional nucleotides or amino acids added together. The term "materially altered," as applied to polynucleotides of the invention, refers to an increase or decrease in ability to express the encoded polypeptide of at least about 50% or more as compared to the expression level of a polynucleotide consisting of the recited sequence. The term "materially altered," as applied to polypeptides of the invention, refers to an increase or decrease in biological activity of at least about 50% or more as compared to the activity of a polypeptide consisting of the recited sequence.

The term "parvovirus" as used herein encompasses the family Parvoviridae, including autonomously-replicating parvoviruses and dependoviruses. The autonomous parvoviruses include members of the genera Parvovirus, Erythrovirus, Densovirus, Iteravirus, and Contravirus. Exemplary autonomous parvoviruses include, but are not limited to, minute virus of mouse, bovine parvovirus, canine parvovirus, chicken parvovirus, feline panleukopenia virus, feline parvovirus, goose parvovirus, H1 parvovirus, muscovy duck parvovirus, snake parvovirus, and B19 virus. Other autonomous parvoviruses are known to those skilled in the art. See, e.g., FIELDS et al., VIROLOGY, volume 2, chapter 69 (4th ed., Lippincott-Raven Publishers).

The genus Dependovirus contains the adeno-associated viruses (AAV), including but not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, avian AAV, bovine AAV, canine AAV, goat AAV, snake AAV, equine AAV, and ovine AAV. See, e.g., FIELDS et al., VIROLOGY, volume 2, chapter 69 (4th ed., Lippincott-Raven Publishers); and Table 1.

The term "adeno-associated virus" (AAV) in the context of the present invention includes without limitation AAV type 1, AAV type 2, AAV type 3 (including types 3A and 3B), AAV type 4, AAV type 5, AAV type 6, AAV type 7, AAV type 8, AAV type 9, AAV type 10, AAV type 11, avian AAV, bovine AAV, canine AAV, equine AAV, and ovine AAV and any other AAV now known or later discovered. See, e.g., BERNARD N. FIELDS et al., VIROLOGY, volume 2, chapter 69 (4th ed., Lippincott-Raven Publishers). A number of additional AAV serotypes and clades have been identified (see, e.g., Gao et al., (2004) J. Virol. 78:6381-6388 and Table 1), which are also encompassed by the term "AAV."

The parvovirus particles and genomes of the present invention can be from, but are not limited to, AAV. The genomic sequences of various serotypes of AAV and the autonomous parvoviruses, as well as the sequences of the native ITRs, Rep proteins, and capsid subunits are known in the art. Such sequences may be found in the literature or in public databases such as GenBank. See, e.g., GenBank Accession Numbers NC_002077, NC_001401, NC_001729, NC_001863, NC_001829, NC_001862, NC_000883, NC_001701, NC_001510, NC_006152, NC_006261, AF063497, U89790, AF043303, AF028705, AF028704, J02275, J01901, J02275, X01457, AF288061, AH009962, AY028226, AY028223, AY631966, AX753250, EU285562, NC_001358, NC_001540, AF513851, AF513852 and AY530579; the disclosures of which are incorporated by reference herein for teaching parvovirus and AAV nucleic acid and amino acid sequences. See also, e.g., Bantel-Schaal et al., (1999) J. Virol. 73: 939; Chiorini et al., (1997) J. Virol. 71:6823; Chiorini et al., (1999) J. Virol. 73:1309; Gao et al., (2002) Proc. Nat. Acad. Sci. USA 99:11854; Moris et al., (2004) Virol. 33-:375-383; Mori et al., (2004) Virol. 330: 375; Muramatsu et al., (1996) Virol. 221:208; Ruffing et al., (1994) J. Gen. Virol. 75:3385; Rutledge et al., (1998) J. Virol. 72:309; Schmidt et al., (2008) J. Virol. 82:8911; Shade et al., (1986) J. Virol. 58:921; Srivastava et al., (1983) J Virol. 45:555; Xiao et al., (1999) J. Virol. 73:3994; international patent publications WO 00/28061, WO 99/61601, WO 98/11244; and U.S. Pat. No. 6,156,303; the disclosures of which are incorporated by reference herein for teaching parvovirus and AAV nucleic acid and amino acid sequences. See also Table 1. An early description of the AAV1, AAV2 and AAV3 ITR sequences is provided by Xiao, X., (1996), "Characterization of Adeno-associated virus (AAV) DNA replication and integration," Ph.D. Dissertation, University of Pittsburgh, Pittsburgh, PA (incorporated herein it its entirety).

A "chimeric" AAV nucleic acid capsid coding sequence or AAV capsid protein is one that combines portions of two or more capsid sequences. A "chimeric" AAV virion or particle comprises a chimeric AAV capsid protein.

The term "tropism" as used herein refers to preferential entry of the virus into certain cell or tissue type(s) and/or preferential interaction with the cell surface that facilitates entry into certain cell or tissue types, optionally and preferably followed by expression (e.g., transcription and, optionally, translation) of sequences carried by the viral genome in the cell, e.g., for a recombinant virus, expression of the heterologous nucleotide sequence(s). Those skilled in the art will appreciate that transcription of a heterologous nucleic acid sequence from the viral genome may not be initiated in the absence of trans-acting factors, e.g., for an inducible promoter or otherwise regulated nucleic acid sequence. In the case of a rAAV genome, gene expression from the viral genome may be from a stably integrated provirus and/or from a non-integrated episome, as well as any other form which the virus nucleic acid may take within the cell.

TABLE 1

| | GenBank Accession Number |
|---|---|
| Complete Genomes | |
| Adeno-associated virus 1 | NC_002077, AF063497 |
| Adeno-associated virus 2 | NC_001401 |
| Adeno-associated virus 3 | NC_001729 |
| Adeno-associated virus 3B | NC_001863 |
| Adeno-associated virus 4 | NC_001829 |
| Adeno-associated virus 5 | Y18065, AF085716 |
| Adeno-associated virus 6 | NC_001862 |
| Avian AAV ATCC VR-865 | AY186198, AY629583, NC_004828 |
| Avian AAV strain DA-1 | NC_006263, AY629583 |
| Bovine AAV | NC_005889, AY388617 |
| Clade A | |
| AAV1 | NC_002077, AF063497 |
| AAV6 | NC_001862 |
| Hu.48 | AY530611 |
| Hu 43 | AY530606 |
| Hu 44 | AY530607 |
| Hu 46 | AY530609 |
| Clade B | |
| Hu. 19 | AY530584 |
| Hu. 20 | AY530586 |
| Hu 23 | AY530589 |
| Hu22 | AY530588 |
| Hu24 | AY530590 |
| Hu21 | AY530587 |
| Hu27 | AY530592 |
| Hu28 | AY530593 |
| Hu 29 | AY530594 |
| Hu63 | AY530624 |
| Hu64 | AY530625 |
| Hu13 | AY530578 |
| Hu56 | AY530618 |
| Hu57 | AY530619 |
| Hu49 | AY530612 |
| Hu58 | AY530620 |
| Hu34 | AY530598 |

TABLE 1-continued

| | GenBank Accession Number |
|---|---|
| Hu35 | AY530599 |
| AAV2 | NC_001401 |
| Hu45 | AY530608 |
| Hu47 | AY530610 |
| Hu51 | AY530613 |
| Hu52 | AY530614 |
| Hu T41 | AY695378 |
| Hu S17 | AY695376 |
| Hu T88 | AY695375 |
| Hu T71 | AY695374 |
| Hu T70 | AY695373 |
| Hu T40 | AY695372 |
| Hu T32 | AY695371 |
| Hu T17 | AY695370 |
| Hu LG15 | AY695377 |
| Clade C | |
| Hu9 | AY530629 |
| Hu10 | AY530576 |
| Hu11 | AY530577 |
| Hu53 | AY530615 |
| Hu55 | AY530617 |
| Hu54 | AY530616 |
| Hu7 | AY530628 |
| Hu18 | AY530583 |
| Hu15 | AY530580 |
| Hu16 | AY530581 |
| Hu25 | AY530591 |
| Hu60 | AY530622 |
| Ch5 | AY243021 |
| Hu3 | AY530595 |
| Hu1 | AY530575 |
| Hu4 | AY530602 |
| Hu2 | AY530585 |
| Hu61 | AY530623 |
| Clade D | |
| Rh62 | AY530573 |
| Rh48 | AY530561 |
| Rh54 | AY530567 |
| Rh55 | AY530568 |
| Cy2 | AY243020 |
| AAV7 | AF513851 |
| Rh35 | AY243000 |
| Rh37 | AY242998 |
| Rh36 | AY242999 |
| Cy6 | AY243016 |
| Cy4 | AY243018 |
| Cy3 | AY243019 |
| Cy5 | AY243017 |
| Rh13 | AY243013 |
| Clade E | |
| Rh38 | AY530558 |
| Hu66 | AY530626 |
| Hu42 | AY530605 |
| Hu67 | AY530627 |
| Hu40 | AY530603 |
| Hu41 | AY530604 |
| Hu37 | AY530600 |
| Rh40 | AY530559 |
| Rh2 | AY243007 |
| Bb1 | AY243023 |
| Bb2 | AY243022 |
| Rh10 | AY243015 |
| Hu17 | AY530582 |
| Hu6 | AY530621 |
| Rh25 | AY530557 |
| Pi2 | AY530554 |
| Pi1 | AY530553 |
| Pi3 | AY530555 |
| Rh57 | AY530569 |
| Rh50 | AY530563 |
| Rh49 | AY530562 |
| Hu39 | AY530601 |
| Rh58 | AY530570 |
| Rh61 | AY530572 |
| Rh52 | AY530565 |

TABLE 1-continued

| | GenBank Accession Number |
|---|---|
| Rh53 | AY530566 |
| Rh51 | AY530564 |
| Rh64 | AY530574 |
| Rh43 | AY530560 |
| AAV8 | AF513852 |
| Rh8 | AY242997 |
| Rh1 | AY530556 |
| Clade F | |
| Hu14 (AAV9) | AY530579 |
| Hu31 | AY530596 |
| Hu32 | AY530597 |
| Clonal Isolate | |
| AAV5 | Y18065, AF085716 |
| AAV 3 | NC_001729 |
| AAV 3B | NC_001863 |
| AAV4 | NC_001829 |
| Rh34 | AY243001 |
| Rh33 | AY243002 |
| Rh32 | AY243003 |

The term "tropism profile" refers to the pattern of transduction of one or more target cells, tissues and/or organs. Representative examples of chimeric AAV capsids have a tropism profile characterized by efficient transduction of cells of the CNS with only low transduction of peripheral organs.

The term "disorder associated with aberrant expression of a CLN1 gene" as used herein refers to a disease, disorder, syndrome, or condition that is caused by or a symptom of decreased or altered expression of the CLN1 gene in a subject relative to the expression level or activity in a normal subject or in a population.

As used herein, "transduction" of a cell by a virus vector (e.g., an AAV vector) means entry of the vector into the cell and transfer of genetic material into the cell by the incorporation of nucleic acid into the virus vector and subsequent transfer into the cell via the virus vector.

Unless indicated otherwise, "efficient transduction" or "efficient tropism," or similar terms, can be determined by reference to a suitable positive or negative control (e.g., at least about 50%, 60%, 70%, 80%, 85%, 90%, 95% or more of the transduction or tropism, respectively, of a positive control or at least about 110%, 120%, 150%, 200%, 300%, 500%, 1000% or more of the transduction or tropism, respectively, of a negative control).

Similarly, it can be determined if a virus "does not efficiently transduce" or "does not have efficient tropism" for a target tissue, or similar terms, by reference to a suitable control. In particular embodiments, the virus vector does not efficiently transduce (i.e., does not have efficient tropism for) tissues outside the CNS, e.g., liver, kidney, gonads and/or germ cells. In particular embodiments, undesirable transduction of tissue(s) (e.g., liver) is 20% or less, 10% or less, 5% or less, 1% or less, 0.1% or less of the level of transduction of the desired target tissue(s) (e.g., CNS cells).

The terms "5' portion" and "3' portion" are relative terms to define a spatial relationship between two or more elements. Thus, for example, a "3' portion" of a polynucleotide indicates a segment of the polynucleotide that is downstream of another segment. The term "3' portion" is not intended to indicate that the segment is necessarily at the 3' end of the polynucleotide, or even that it is necessarily in the 3' half of the polynucleotide, although it may be. Likewise, a "5' portion" of a polynucleotide indicates a segment of the polynucleotide that is upstream of another segment. The term "5' portion" is not intended to indicate that the segment is necessarily at the 5' end of the polynucleotide, or even that it is necessarily in the 5' half of the polynucleotide, although it may be.

As used herein, the term "polypeptide" encompasses both peptides and proteins, unless indicated otherwise. The term "fragment" of a given peptide as used herein is meant to refer to any peptide subset of the peptide. In one embodiment, a fragment comprises at least 2 contiguous amino acids of the sequence of the peptide. In another embodiment, the fragment comprises at least 4, at least 5, at least 6, at least 8, at least 10, at least 20, at least 30, at least 40, at least 50, at least 60, at least 70, at least 80, at least 90, or at least 100 contiguous amino acids of the peptide. In some embodiments, the fragment has at least 5%, 10%, 20%, 30%, 40%, 50%, 60%, 70%, 80%, or 90% sequence of a given peptide.

A "polynucleotide," "nucleic acid," or "nucleotide sequence" is a sequence of nucleotide bases, and may be RNA, DNA or DNA-RNA hybrid sequences (including both naturally occurring and non-naturally occurring nucleotide), but is preferably either a single or double stranded DNA sequence.

The term "open reading frame (ORF)," as used herein, refers to the portion of a polynucleotide, e.g., a gene, that encodes a polypeptide.

The term "codon-optimized," as used herein, refers to a coding sequence that is optimized relative to a wild type coding sequence (e.g., a coding sequence for PPT1) to increase expression of the coding sequence by substituting one or more codons normally present in the coding sequence with a codon for the same (synonymous) amino acid. In some embodiments, the substitutions minimize rare codons (e.g., human codons), increase total GC content, decrease CpG content, remove cryptic splice donor or acceptor sites, and/or add or remove ribosomal entry sites, such as Kozak sequences.

The term "sequence identity," as used herein, has the standard meaning in the art. As is known in the art, a number of different programs can be used to identify whether a polynucleotide or polypeptide has sequence identity or similarity to a known sequence. Sequence identity or similarity may be determined using standard techniques known in the art, including, but not limited to, the local sequence identity algorithm of Smith & Waterman, *Adv. Appl. Math.* 2:482 (1981), by the sequence identity alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Drive, Madison, WI), the Best Fit sequence program described by Devereux et al., *Nucl. Acid Res.* 12:387 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351 (1987); the method is similar to that described by Higgins & Sharp, *CABIOS* 5:151 (1989).

Another example of a useful algorithm is the BLAST algorithm, described in Altschul et al., *J. Mol. Biol.* 215:403 (1990) and Karlin et al., *Proc. Natl. Acad. Sci. USA* 90:5873 (1993). A particularly useful BLAST program is the WU-BLAST-2 program which was obtained from Altschul et al.,

*Meth. Enzymol.*, 266:460 (1996); blast.wustl/edu/blast/RE-ADME.html. WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., *Nucleic Acids Res.* 25:3389 (1997).

A percentage amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, percent nucleic acid sequence identity is defined as the percentage of nucleotide residues in the candidate sequence that are identical with the nucleotides in the polynucleotide specifically disclosed herein.

The alignment may include the introduction of gaps in the sequences to be aligned. In addition, for sequences which contain either more or fewer nucleotides than the polynucleotides specifically disclosed herein, it is understood that in one embodiment, the percentage of sequence identity will be determined based on the number of identical nucleotides in relation to the total number of nucleotides. Thus, for example, sequence identity of sequences shorter than a sequence specifically disclosed herein, will be determined using the number of nucleotides in the shorter sequence, in one embodiment. In percent identity calculations relative weight is not assigned to various manifestations of sequence variation, such as insertions, deletions, substitutions, etc.

In one embodiment, only identities are scored positively (+1) and all forms of sequence variation including gaps are assigned a value of "0," which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

As used herein, an "isolated" nucleic acid or nucleotide sequence (e.g., an "isolated DNA" or an "isolated RNA") means a nucleic acid or nucleotide sequence separated or substantially free from at least some of the other components of the naturally occurring organism or virus, for example, the cell or viral structural components or other polypeptides or nucleic acids commonly found associated with the nucleic acid or nucleotide sequence.

Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide.

As used herein, the term "modified," as applied to a polynucleotide or polypeptide sequence, refers to a sequence that differs from a wild-type sequence due to one or more deletions, additions, substitutions, or any combination thereof.

As used herein, to "isolate" or "purify" (or grammatical equivalents) a virus vector, it is meant that the virus vector is at least partially separated from at least some of the other components in the starting material.

By the term "treat," "treating," or "treatment of" (or grammatically equivalent terms) it is meant that the severity of the subject's condition is reduced or at least partially improved or ameliorated and/or that some alleviation, mitigation or decrease in at least one clinical symptom is achieved and/or there is a delay in the progression of the condition.

As used herein, the term "prevent," "prevents," or "prevention" (and grammatical equivalents thereof) refers to a delay in the onset of a disease or disorder or the lessening of symptoms upon onset of the disease or disorder. The terms are not meant to imply complete abolition of disease and encompasses any type of prophylactic treatment that reduces the incidence of the condition or delays the onset and/or progression of the condition.

A "treatment effective" amount as used herein is an amount that is sufficient to provide some improvement or benefit to the subject. Alternatively stated, a "treatment effective" amount is an amount that will provide some alleviation, mitigation, decrease or stabilization in at least one clinical symptom in the subject. Those skilled in the art will appreciate that the therapeutic effects need not be complete or curative, as long as some benefit is provided to the subject.

A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

A "heterologous nucleotide sequence" or "heterologous nucleic acid" is a sequence that is not naturally occurring in the virus. Generally, the heterologous nucleic acid or nucleotide sequence comprises an open reading frame that encodes a polypeptide and/or a nontranslated RNA.

As used herein, the term "vector" or "delivery vector" (and similar terms) refers to a DNA fragment, a nucleotide molecule, or a particle that is capable of delivery to a cell or subject. The vector includes a viral or non-viral vector. In one embodiment, the vector comprises bacterial plasmid, phage, yeast plasmid, plant cell virus, mammalian cell viral vector, or other vectors. In another embodiment, the vector comprises a nanoparticle. The term "virus vector," or "viral vector" generally refers to a virus particle that functions as a nucleic acid delivery vehicle, and which comprises the viral nucleic acid (i.e., the vector genome) packaged within the virion. Virus vectors according to the present invention include but are not limited to a chimeric AAV capsid according to the invention and can package an AAV or rAAV genome or any other nucleic acid including viral nucleic acids. Alternatively, in some contexts, the term "vector," "virus vector," "delivery vector" (and similar terms) may be used to refer to the vector genome (e.g., vDNA) in the absence of the virion and/or to a viral capsid that acts as a transporter to deliver molecules tethered to the capsid or packaged within the capsid. The term "non-viral vector" refers to a vector, a plasmid, a construct, a molecule, or a particle that does not include a viral element. The non-viral particle, in some embodiments, comprises, consists essentially of, or consists of a bacterial plasmid, a yeast plasmid, a recombinant vector, a nanoparticle, or other vectors. In one embodiment, the non-viral particle comprises a nanoparticle. The non-viral vectors can be delivered to a cell or a subject with various methods, which include but are not limited to injection, electroporation, gene gun, sonoporation, magnetofection, hydrodynamic delivery, or other physical or chemical methods.

The virus vectors of the invention can further be duplexed parvovirus particles as described in international patent publication WO 01/92551 (the disclosure of which is incorporated herein by reference in its entirety). Thus, in some embodiments, double stranded (duplex) genomes can be packaged.

A "recombinant AAV vector genome" or "rAAV genome" is an AAV genome (i.e., vDNA) that comprises at least one inverted terminal repeat (e.g., one, two or three inverted terminal repeats) and one or more heterologous nucleotide sequences. rAAV vectors generally retain the 145 base terminal repeat(s) (TR(s)) in cis to generate virus; however, modified AAV TRs and non-AAV TRs including partially or completely synthetic sequences can also serve this purpose. All other viral sequences are dispensable and may be supplied in trans (Muzyczka, (1992) *Curr. Topics Microbiol. Immunol.* 158:97). The rAAV vector optionally comprises two TRs (e.g., AAV TRs), which generally will be at the 5' and 3' ends of the heterologous nucleotide sequence(s), but need not be contiguous thereto. The TRs can be the same or different from each other. The vector genome can also contain a single ITR at its 3' or 5' end.

The term "terminal repeat" or "TR" includes any viral terminal repeat or synthetic sequence that forms a hairpin structure and functions as an inverted terminal repeat (i.e., mediates the desired functions such as replication, virus packaging, integration and/or provirus rescue, and the like). The TR can be an AAV TR or a non-AAV TR. For example, a non-AAV TR sequence such as those of other parvoviruses (e.g., canine parvovirus (CPV), mouse parvovirus (MVM), human parvovirus B-19) or the SV40 hairpin that serves as the origin of SV40 replication can be used as a TR, which can further be modified by truncation, substitution, deletion, insertion and/or addition. Further, the TR can be partially or completely synthetic, such as the "double-D sequence" as described in U.S. Pat. No. 5,478,745 to Samulski et al.

Parvovirus genomes have palindromic sequences at both their 5' and 3' ends. The palindromic nature of the sequences leads to the formation of a hairpin structure that is stabilized by the formation of hydrogen bonds between the complementary base pairs. This hairpin structure is believed to adopt a "Y" or a "T" shape. See, e.g., FIELDS et al., VIROLOGY, volume 2, chapters 69 & 70 (4th ed., Lippincott-Raven Publishers).

An "AAV terminal repeat" or "AAV TR" may be from any AAV, including but not limited to serotypes 1, 2, 3, 4, 5, 6, 7, 8, 9, 10 or 11 or any other AAV now known or later discovered (see, e.g., Table 1). In some embodiments, the AAV terminal repeat does not have the native terminal repeat sequence (e.g., a native AAV TR sequence may be altered by insertion, deletion, truncation and/or missense mutations), when the terminal repeat mediates the desired functions, e.g., replication, virus packaging, integration, and/or provirus rescue, and the like. In another embodiment, the AAV terminal repeat has the native terminal repeat sequence.

The terms "rAAV particle" and "rAAV virion" are used interchangeably here. A "rAAV particle" or "rAAV virion" comprises a rAAV vector genome packaged within an AAV capsid.

The virus vectors of the invention can further be "targeted" virus vectors (e.g., having a directed tropism) and/or a "hybrid" parvovirus (i.e., in which the viral ITRs and viral capsid are from different parvoviruses) as described in international patent publication WO 00/28004 and Chao et al., (2000) *Mol. Therapy* 2:619.

Further, the viral capsid or genomic elements can contain other modifications, including insertions, deletions and/or substitutions.

As used herein, the term "amino acid" encompasses any naturally occurring amino acids, modified forms thereof, and synthetic amino acids.

Naturally occurring, levorotatory (L-) amino acids are shown in Table 2.

TABLE 2

| Amino Acid Residue | Abbreviation | |
|---|---|---|
| | Three-Letter Code | One-Letter Code |
| Alanine | Ala | A |
| Arginine | Arg | R |
| Asparagine | Asn | N |
| Aspartic acid (Aspartate) | Asp | D |
| Cysteine | Cys | C |
| Glutamine | Gln | Q |
| Glutamic acid (Glutamate) | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Alternatively, the amino acid can be a modified amino acid residue (nonlimiting examples are shown in Table 3) or can be an amino acid that is modified by post-translation modification (e.g., acetylation, amidation, formylation, hydroxylation, methylation, phosphorylation or sulfatation).

TABLE 3

Amino Acid Residue Derivatives

| Modified Amino Acid Residue | Abbreviation |
|---|---|
| 2-Aminoadipic acid | Aad |
| 3-Aminoadipic acid | bAad |
| beta-Alanine, beta-Aminoproprionic acid | bAla |
| 2-Aminobutyric acid | Abu |
| 4-Aminobutyric acid, Piperidinic acid | 4Abu |
| 6-Aminocaproic acid | Acp |
| 2-Aminoheptanoic acid | Ahe |
| 2-Aminoisobutyric acid | Aib |
| 3-Aminoisobutyric acid | bAib |
| 2-Aminopimelic acid | Apm |
| t-butylalanine | t-BuA |
| Citrulline | Cit |
| Cyclohexylalanine | Cha |
| 2,4-Diaminobutyric acid | Dbu |
| Desmosine | Des |
| 2,2'-Diaminopimelic acid | Dpm |
| 2,3-Diaminoproprionic acid | Dpr |
| N-Ethylglycine | EtGly |
| N-Ethylasparagine | EtAsn |
| Homoarginine | hArg |
| Homocysteine | hCys |
| Homoserine | hSer |
| Hydroxylysine | Hyl |
| Allo-Hydroxylysine | aHyl |

TABLE 3-continued

Amino Acid Residue Derivatives

| Modified Amino Acid Residue | Abbreviation |
|---|---|
| 3-Hydroxyproline | 3Hyp |
| 4-Hydroxyproline | 4Hyp |
| Isodesmosine | Ide |
| allo-Isoleucine | aIle |
| Methionine sulfoxide | MSO |
| N-Methylglycine, sarcosine | MeGly |
| N-Methylisoleucine | MeIle |
| 6-N-Methyllysine | MeLys |
| N-Methylvaline | MeVal |
| 2-Naphthylalanine | 2-Nal |
| Norvaline | Nva |
| Norleucine | Nle |
| Ornithine | Orn |
| 4-Chlorophenylalanine | Phe(4-Cl) |
| 2-Fluorophenylalanine | Phe(2-F) |
| 3-Fluorophenylalanine | Phe(3-F) |
| 4-Fluorophenylalanine | Phe(4-F) |
| Phenylglycine | Phg |
| Beta-2-thienylalanine | Thi |

Further, the non-naturally occurring amino acid can be an "unnatural" amino acid as described by Wang et al., (2006) Annu. Rev. Biophys. Biomol. Struct. 35:225-49. These unnatural amino acids can advantageously be used to chemically link molecules of interest to the AAV capsid protein.

The term "template" or "substrate" is used herein to refer to a polynucleotide sequence that may be replicated to produce the parvovirus viral DNA. For the purpose of vector production, the template will typically be embedded within a larger nucleotide sequence or construct, including but not limited to a plasmid, naked DNA vector, bacterial artificial chromosome (BAC), yeast artificial chromosome (YAC) or a viral vector (e.g., adenovirus, herpesvirus, Epstein-Barr Virus, AAV, baculoviral, retroviral vectors, and the like). Alternatively, the template may be stably incorporated into the chromosome of a packaging cell.

As used herein, parvovirus or AAV "Rep coding sequences" indicate the nucleic acid sequences that encode the parvoviral or AAV non-structural proteins that mediate viral replication and the production of new virus particles. The parvovirus and AAV replication genes and proteins have been described in, e.g., FIELDS et al., VIROLOGY, volume 2, chapters 69 & 70 (4th ed., Lippincott-Raven Publishers).

The "Rep coding sequences" need not encode all of the parvoviral or AAV Rep proteins. For example, with respect to AAV, the Rep coding sequences do not need to encode all four AAV Rep proteins (Rep78, Rep 68, Rep52 and Rep40), in fact, it is believed that AAV5 only expresses the spliced Rep68 and Rep40 proteins. In representative embodiments, the Rep coding sequences encode at least those replication proteins that are necessary for viral genome replication and packaging into new virions. The Rep coding sequences will generally encode at least one large Rep protein (i.e., Rep78/68) and one small Rep protein (i.e., Rep52/40). In particular embodiments, the Rep coding sequences encode the AAV Rep78 protein and the AAV Rep52 and/or Rep40 proteins. In other embodiments, the Rep coding sequences encode the Rep68 and the Rep52 and/or Rep40 proteins. In a still further embodiment, the Rep coding sequences encode the Rep68 and Rep52 proteins, Rep68 and Rep40 proteins, Rep78 and Rep52 proteins, or Rep78 and Rep40 proteins.

As used herein, the term "large Rep protein" refers to Rep68 and/or Rep78. Large Rep proteins of the claimed invention may be either wild-type or synthetic. A wild-type large Rep protein may be from any parvovirus or AAV, including but not limited to serotypes 1, 2, 3a, 3b, 4, 5, 6, 7, 8, 9, 10, 11, or 13, or any other AAV now known or later discovered (see, e.g., Table 1). A synthetic large Rep protein may be altered by insertion, deletion, truncation and/or missense mutations.

Those skilled in the art will further appreciate that it is not necessary that the replication proteins be encoded by the same polynucleotide. For example, for MVM, the NS-1 and NS-2 proteins (which are splice variants) may be expressed independently of one another. Likewise, for AAV, the p19 promoter may be inactivated and the large Rep protein(s) expressed from one polynucleotide and the small Rep protein(s) expressed from a different polynucleotide. Typically, however, it will be more convenient to express the replication proteins from a single construct. In some systems, the viral promoters (e.g., AAV p19 promoter) may not be recognized by the cell, and it is therefore necessary to express the large and small Rep proteins from separate expression cassettes. In other instances, it may be desirable to express the large Rep and small Rep proteins separately, i.e., under the control of separate transcriptional and/or translational control elements. For example, it may be desirable to control expression of the large Rep proteins, so as to decrease the ratio of large to small Rep proteins. In the case of insect cells, it may be advantageous to down-regulate expression of the large Rep proteins (e.g., Rep78/68) to avoid toxicity to the cells (see, e.g., Urabe et al., (2002) *Human Gene Therapy* 13:1935).

As used herein, the parvovirus or AAV "cap coding sequences" encode the structural proteins that form a functional parvovirus or AAV capsid (i.e., can package DNA and infect target cells). Typically, the cap coding sequences will encode all of the parvovirus or AAV capsid subunits, but less than all of the capsid subunits may be encoded as long as a functional capsid is produced. Typically, but not necessarily, the cap coding sequences will be present on a single nucleic acid molecule.

The capsid structure of autonomous parvoviruses and AAV are described in more detail in BERNARD N. FIELDS et al., VIROLOGY, volume 2, chapters 69 & 70 (4th ed., Lippincott-Raven Publishers).

By "substantially retain" a property, it is meant that at least about 75%, 85%, 90%, 95%, 97%, 98%, 99% or 100% of the property (e.g., activity or other measurable characteristic) is retained.

CLN1 Expression Cassettes and Vectors

The present invention relates to the design of a CLN1 expression cassette to provide maximal expression of palmitoyl protein thioesterase 1 (PPT1), the enzyme encoded by the CLN1 gene, and the use of the expression cassette to achieve therapeutic levels of PPT1 in a subject.

Thus, one aspect of the invention relates to a polynucleotide comprising a nucleotide sequence encoding a palmitoyl protein thioesterase 1 (PPT1) polypeptide or a fragment thereof, wherein the nucleotide sequence is codon-optimized for expression in human cells. In one embodiment, the polynucleotide comprises the nucleotide sequence comprising a sequence of SEQ ID NO: 1 (or its complement) or a sequence at least about 90% identical thereto, or its complement. In another embodiment, the nucleotide sequence encodes a PPT1 polypeptide or its fragment. The PPT1 polypeptide sequences can be found in GenBank, which include but are not limited to, Accession Nos: NP_071947.1, NP_776579.1, NP_032943.2, AAM49613.1, and AAH08426.1. In another embodiment, the nucleotide sequence is codon-optimized for expression in a cell. The cell includes but is not limited to a human cell, a rat cell, a mouse cell, a dog cell, or any mammal or plant cells. In one embodiment, the cell is a human cell. In another embodiment, the polynucleotide comprises a CLN1 open reading frame of human, rat, mouse, bovine, or any other species. In another embodiment, the polynucleotide comprises a human CLN1 open reading frame. The open reading frame is the portion of the CLN1 gene that encodes for PPT1.

In some embodiments, the codon-optimized CLN1 open reading frame comprises, consists essentially of, or consists of the nucleotide sequence of SEQ ID NO: 1 or a sequence at least about 70% identical thereto, e.g., at least about 70, 75, 80, 85, 90, 91, 92, 93, 94, 95, 96, 97, 98, or 99% identical thereto.

SEQ ID NO: 1: Human codon-optimized CLN1 open
reading frame (added stop codon is underlined)
ATGGCTTCTCCGGGGTGTCTGTGGCTGCTGGCAGTGGCACTCCTTCCCT

GGACTTGCGCCAGCCGGGCTCTGCAGCACCTCGACCCTCCAGCCCCTCT

TCCACTGGTGATTTGGCACGGAATGGGTGATTCCTGCTGTAATCCCCTG

TCAATGGGAGCCATCAAGAAGATGGTGGAGAAGAAGATCCCTGGAATCT

ACGTGCTGTCACTGGAGATTGGAAAGACCCTGATGGAGGACGTCGAGAA

CTCCTTCTTCCTCAATGTCAACTCTCAAGTGACCACCGTCTGCCAGGCC

CTGGCCAAGGACCCGAAGCTGCAGCAGGGGTATAATGCTATGGGGTTCA

GCCAGGGAGGACAGTTCCTTCGGGCTGTGGCCAACGCTGCCCTAGCCC

ACCCATGATCAACCTGATCTCAGTGGGTGGCCAGCATCAGGGCGTGTTC

GGACTTCCCCGGTGTCCCGGGGAATCCTCTCATATCTGCGACTTCATCC

GCAAAACTCTCAATGCAGGCGCTTATTCAAAGGTCGTCCAAGAGAGGCT

GGTGCAAGCCGAGTACTGGCACGATCCCATTAAGGAGGACGTGTACAGA

AATCACTCAATCTTTCTGGCCGACATTAACCAGGAGAGGGGAATTAACG

AATCATATAAGAAGAATCTCATGGCCCTCAAAAAGTTCGTCATGGTGAA

GTTCCTTAACGATAGCATTGTGGACCCAGTGGACAGCGAATGGTTCGGA

TTTTACCGCTCAGGCCAGGCAAAAGAAACCATCCCTCTCCAAGAGACTT

CTCTTTACACCCAAGACAGACTTGGGCTTAAGGAAATGGATAACGCTGG

TCAGCTGGTGTTCCTCGCCACCGAAGGTGACCATCTGCAGCTCAGCGAA

GAGTGGTTCTACGCTCATATCATCCCGTTTCTTGGTTGAT<u>AA</u>

Another aspect of the invention relates to an expression cassette comprising a polynucleotide encoding a PPT1 polypeptide or fragment thereof. In one embodiment, the polynucleotide comprises a CLN1 open reading frame of any species. In another embodiment, the polynucleotide comprises a human CLN1 open reading frame. In certain embodiments, the polynucleotide is a human codon-optimized sequence, e.g., a polynucleotide comprising the nucleotide sequence of SEQ ID NO: 1 or a sequence at least about 70% identical thereto, e.g., at least about 70, 75, 80, 85, 90, 91, 92, 93, 94, 95, 96, 97, 98, or 99% identical thereto.

The polynucleotide in the expression cassette may be operably linked to one or more expression elements that may enhance expression of the encoded polypeptide. In one embodiment, the CLN1 polynucleotide in the expression cassette is operably linked to one or more expression elements that may enhance expression of CLN1. In some embodiments, the polynucleotide is operably linked to a promoter, e.g., a chicken beta-actin promoter, e.g., a promoter comprising, consisting essentially of, or consisting of the nucleotide sequence of SEQ ID NO:2. In some embodiments, the promoter further comprises the chicken beta-actin exon 1 and intron 1, e.g., comprising, consisting essentially of, or consisting of the nucleotide sequence of SEQ ID NO:3.

SEQ ID NO: 2: Chicken beta-actin promoter
TACGTATTAGTCATCGCTATTACCATGGTCGAGGTGAGCCCCACGTTCT

GCTTCACTCTCCCCATCTCCCCCCCCTCCCCACCCCCAATTTTGTATTT

ATTTATTTTTTAATTATTTTGTGCAGCGATGGGGCGGGGGGGGGGGG

GGGCGCGCGCCAGGCGGGGCGGGGCGGGGCGAGGGGCGGGGCGGGGCGA

GGCGGAGAGGTGCGGCGGCAGCCAATCAGAGCGGCGCGCTCCGAAAGTT

TCCTTTTATGGCGAGGCGGCGGCGGCGGCGGCCCTATAAAAAGCGAAGC

GCGCGGCGGGCG

SEQ ID NO: 3: Chicken beta-actin exon 1 and
intron 1
GGAGTCGCTGCGACGCTGCCTTCGCCCCGTGCCCCGCTCCGCCGCCGCC

TCGCGCCGCCCGCCCCGGCTCTGACTGACCGCGTTACTCCCACAGGTGA

GCGGGCGGGACGGCCCTTCTCCTCCGGGCTGTAATTAGC

In some embodiments, the polynucleotide is operably linked to an enhancer, e.g., a cytomegalovirus enhancer, e.g., an enhancer comprising, consisting essentially of, or consisting of the nucleotide sequence of SEQ ID NO:4.

SEQ ID NO: 4: Cytomegalovirus enhancer
TACATAACTTACGGTAAATGGCCCGCCTGGCTGACCGCCCAACGACCCC

CGCCCATTGACGTCAATAGTAACGCCAATAGGGACTTTCCATTGACGTC

AATGGGTGGAGTATTTACGGTAAACTGCCCACTTGGCAGTACATCAAGT

GTATCATATGCCAAGTACGCCCCCTATTGACGTCAATGACGGTAAATGG

CCCGCCTGGCATTGTGCCCAGTACATGACCTTATGGGACTTTCCTACTT

GGCAGTACATC

In some embodiments, the polynucleotide is operably linked to an intron, e.g., a hybrid/modified MVM intron, e.g., an intron comprising, consisting essentially of, or consisting of the nucleotide sequence of SEQ ID NO:5. The intron, may be located in any part of the expression cassette where it is effective to enhance expression, e.g., preceding the ORF, within the ORF, or between the ORF and the polyadenylation site.

SEQ ID NO: 5: Hybrid/modified MVM intron
AAGAGGTAAGGGTTTAAGGGATGGTTGGTTGGTGGGGTATTAATGTTTA

ATTACCTGGAGCACCTGCCTGAAATCACTTTTTTTCAGGTTGG

In some embodiments, the polynucleotide is operably linked to a polyadenylation signal, e.g., a bovine growth hormone polyadenylation signal, e.g., a polyadenylation signal comprising, consisting essentially of, or consisting of the nucleotide sequence of SEQ ID NO:6.

SEQ ID NO: 6: Bovine growth hormone
polyadenylation signal
CTCGACTGTGCCTTCTAGTTGCCAGCCATCTGTTGTTTGCCCCTCCCCC

GTGCCTTCCTTGACCCTGGAAGGTGCCACTCCCACTGTCCTTTCCTAAT

AAAATGAGGAAATTGCATCGCATTGTCTGAGTAGGTGTCATTCTATTCT

GGGGGGTGGGGTGGGGCAGGACAGCAAGGGGGAGGATTGGGAAGACAAC

AGCAGGCATGCTGGGGATGCGGTGGGCTCTATGGCTTCTGAGGCGGAAA

GAACCAGCT

Those skilled in the art will further appreciate that a variety of promoter/enhancer elements may be used depending on the level and tissue-specific expression desired. The term "promoter" as used herein indicates a DNA region to which an RNA polymerase binds to initiate the transcription of a nucleic acid sequence (e.g., a gene) which is operably linked to the promoter. The promoter can be a viral or non-viral promoter. The viral promoter includes but is not limited to pCMV, SV40, MMTV promoters. The non-viral promoter includes but is not limited to UbC, EF, or PGK promoters. The term "enhancer" refers to a cis-acting transcriptional regulatory element. In one embodiment, the enhancer confers an aspect of the overall modulation of gene expression. In another embodiment, the enhancer elements bind DNA-binding proteins and/or affect DNA topology, producing local conformations that selectively allow or restrict access of RNA polymerase to the DNA template or that facilitate selective opening of the double helix at the site of transcriptional initiation. The non-limiting list of enhancers can be found at VISTA Enhancer Browser, which is available at enhancer.lbl.gov/?. The term "intron" refers to an untranslated DNA sequence between exons, together with 5' and 3' untranslated regions associated with a genetic locus. The promoter/enhancer may be constitutive or inducible, depending on the pattern of expression desired. The promoter/enhancer may be native or foreign and can be a natural or a synthetic sequence. By foreign, it is intended that the transcriptional initiation region is not found in the wild-type host into which the transcriptional initiation region is introduced.

Promoter/enhancer elements can be native to the target cell or subject to be treated and/or native to the heterologous nucleic acid sequence. The promoter/enhancer element is generally chosen so that it will function in the target cell(s) of interest. In representative embodiments, the promoter/enhancer element is a mammalian promoter/enhancer element. The promoter/enhance element may be constitutive or inducible.

Inducible expression control elements are generally used in those applications in which it is desirable to provide regulation over expression of the heterologous nucleic acid sequence(s). Inducible promoters/enhancer elements for gene delivery can be tissue-specific or tissue-preferred promoter/enhancer elements, and include muscle specific or preferred (including cardiac, skeletal and/or smooth muscle), neural tissue specific or preferred (including brain-specific), eye (including retina-specific and cornea-specific), liver specific or preferred, bone marrow specific or preferred, pancreatic specific or preferred, spleen specific or preferred, and lung specific or preferred promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In embodiments wherein the CLN1 ORF is transcribed and then translated in the target cells, specific initiation signals are generally employed for efficient translation of inserted protein coding sequences. These exogenous translational control sequences, which may include the ATG initiation codon and adjacent sequences, can be of a variety of origins, both natural and synthetic.

In certain embodiments, the expression cassette further comprises at least one adeno-associated virus (AAV) inverted terminal repeat (ITR), e.g., two AAV ITRs. The two ITRs may have the same nucleotide sequence or different nucleotide sequences. The AAV ITRs may be from any AAV serotype, e.g., AAV2. Each ITR independently may be the wild-type sequence or a modified sequence. In some embodiments, the expression cassette is an AAV genome, e.g., a self-complementary AAV genome.

In certain embodiments, the expression cassette comprises a polynucleotide encoding a PPT1 polypeptide or a fragment thereof. In one embodiment, the expression cassette comprises a human CLN1 open reading frame and any combination of one or more of a promoter, exon, intron, enhancer, and polyadenylation signal. In certain embodiments, the expression cassette comprises a polynucleotide comprising a human CLN1 open reading frame and any combination of one or more of a promoter, exon, intron, enhancer, and polyadenylation signal. In certain embodiments, the expression cassette comprises an enhancer, a promoter, an intron, a human CLN1 open reading frame, and a polyadenylation site, optionally in the recited order. In certain embodiments, the expression cassette comprises an AAV ITR, an enhancer, a promoter, an intron, a human CLN1 open reading frame, a polyadenylation site, and an AAV ITR, optionally in the recited order. In certain embodiments, the expression cassette comprises a CMV enhancer, a chicken beta actin promoter, a hybrid/modified MVM intron, a human CLN1 open reading frame, and a bovine growth hormone polyadenylation site, optionally in the recited order. In certain embodiments, the expression cassette comprises a mutant AAV ITR, a CMV enhancer, a chicken beta actin promoter, a hybrid/modified MVM intron, a human CLN1 open reading frame, a bovine growth hormone polyadenylation site, and a wild-type AAV ITR, optionally in the recited order.

In some embodiments, the expression cassette comprise, consists essentially of, or consists of the nucleotide sequence of SEQ ID NO: 7 or a sequence at least about 70% identical thereto, e.g., at least about 70, 75, 80, 85, 90, 91, 92, 93, 94, 95, 96, 97, 98, or 99% identical thereto.

SEQ ID NO: 7: CLN1 expression cassette
CTGCGCGCTCGCTCGCTCACTGAGGCCGCCCGGGCAAAGCCCGGGCGTC

GGGCGACCTTTGGTCGCCCGGCCTCAGTGAGCGAGCGAGCGCGCAGAGA

GGGAGTGGGGTTCGGTACCCGTTACATAACTTACGGTAAATGGCCCGCC

TGGCTGACCGCCCAACGACCCCCGCCCATTGACGTCAATAGTAACGCCA

ATAGGGACTTTCCATTGACGTCAATGGGTGGAGTATTTACGGTAAACTG

CCCACTTGGCAGTACATCAAGTGTATCATATGCCAAGTACGCCCCCTAT

TGACGTCAATGACGGTAAATGGCCCGCCTGGCATTGTGCCCAGTACATG

ACCTTATGGGACTTTCCTACTTGGCAGTACATCTACGTATTAGTCATCG

-continued

```
CTATTACCATGGTCGAGGTGAGCCCCACGTTCTGCTTCACTCTCCCCAT

CTCCCCCCCCTCCCCACCCCCAATTTTGTATTTATTTATTTTTTAATTA

TTTTGTGCAGCGATGGGGCGGGGGGGGGGGGGGGCGCGCGCCAGGCG

GGGCGGGGCGGGGCGAGGGGCGGGGCGGGGCGAGGCGGAGAGGTGCGGC

GGCAGCCAATCAGAGCGGCGCGCTCCGAAAGTTTCCTTTTATGGCGAGG

CGGCGGCGGCGGCGCCCTATAAAAAGCGAAGCGCGCGGCGGGCGGGAG

TCGCTGCGACGCTGCCTTCGCCCCGTGCCCCGCTCCGCCGCCGCCTCGC

GCCGCCCGCCCCGGCTCTGACTGACCGCGTTACTCCCACAGGTGAGCGG

GCGGGACGGCCCTTCTCCTCCGGGCTGTAATTAGCTGAGCAAGAGGTAA

GGGTTTAAGGGATGGTTGGTTGGTGGGGTATTAATGTTTAATTACCTGG

AGCACCTGCCTGAAATCACTTTTTTTCAGGTTGGACCGGTCGCCACCAT

GGCTTCTCCGGGGTGTCTGTGGCTGCTGGCAGTGGCACTCCTTCCCTGG

ACTTGCGCCAGCCGGGCTCTGCAGCACCTCGACCCTCCAGCCCTCTTC

CACTGGTGATTTGGCACGGAATGGGTGATTCCTGCTGTAATCCCCTGTC

AATGGGAGCCATCAAGAAGATGGTGGAGAAGAAGATCCCTGGAATCTAC

GTGCTGTCACTGGAGATTGGAAAGACCCTGATGGAGGACGTCGAGAACT

CCTTCTTCCTCAATGTCAACTCTCAAGTGACCACCGTCTGCCAGGCCCT

GGCCAAGGACCCGAAGCTGCAGCAGGGGTATAATGCTATGGGGTTCAGC

CAGGGAGGACAGTTCCTTCGGGCTGTGGCCCAACGCTGCCCTAGCCCAC

CCATGATCAACCTGATCTCAGTGGGTGGCCAGCATCAGGGCGTGTTCGG

ACTTCCCCGGTGTCCCGGGGAATCCTCTCATATCTGCGACTTCATCCGC

AAAACTCTCAATGCAGGCGCTTATTCAAAGGTCGTCCAAGAGAGGCTGG

TGCAAGCCGAGTACTGGCACGATCCCATTAAGGAGGACGTGTACAGAAA

TCACTCAATCTTTCTGGCCGACATTAACCAGGAGAGGGAATTAACGAA

TCATATAAGAAGAATCTCATGGCCCTCAAAAAGTTCGTCATGGTGAAGT

TCCTTAACGATAGCATTGTGGACCCAGTGGACAGCGAATGGTTCGGATT

TTACCGCTCAGGCCAGGCAAAAGAAACCATCCCTCTCCAAGAGACTTCT

CTTTACACCCAAGACAGACTTGGGCTTAAGGAAATGGATAACGCTGGTC

AGCTGGTGTTCCTCGCCACCGAAGGTGACCATCTGCAGCTCAGCGAAGA

GTGGTTCTACGCTCATATCATCCCGTTTCTTGGTTGATAAGCGGCCGCG

GGGATCCCTCGACTGTGCCTTCTAGTTGCCAGCCATCTGTTGTTTGCCC

CTCCCCCGTGCCTTCCTTGACCCTGGAAGGTGCCACTCCCACTGTCCTT

TCCTAATAAAATGAGGAAATTGCATCGCATTGTCTGAGTAGGTGTCATT

CTATTCTGGGGGGTGGGGTGGGGCAGGACAGCAAGGGGGAGGATTGGGA

AGACAACAGCAGGCATGCTGGGGATGCGGTGGGCTCTATGGCTTCTGAG

GCGGAAAGAACCAGCTTTGGACGCGTAGGAACCCCTAGTGATGGAGTTG

GCCACTCCCTCTCTGCGCGCTCGCTCGCTCACTGAGGCCGGGCGACCAA

AGGTCGCCCGACGCCCGGGCTTTGCCCGGGCGGCCTCAGTGAGCGAGCG

AGCGCGCAGCTGGCGTAATAGCGAAGAGGCCCGCACCGATCGCCCTTC
```

A further aspect of the invention relates to a vector comprising the polynucleotide or the expression cassette of the invention. Suitable vectors include, but are not limited to, a plasmid, phage, viral vector (e.g., an AAV vector, an adenovirus vector, a herpesvirus vector, an alphavirus, or a baculovirus vector), bacterial artificial chromosome (BAC), or yeast artificial chromosome (YAC). For example, the nucleic acid can comprise, consist of, or consist essentially of an AAV vector comprising a 5' and/or 3' terminal repeat (e.g., 5' and/or 3' AAV terminal repeat).

In some embodiments, the vector is a viral vector, e.g., an AAV vector. The AAV vector may be any AAV serotype, e.g., AAV9. In some embodiments, the AAV vector may comprise wild-type capsid proteins. In other embodiments, the AAV vector may comprise a modified capsid protein with altered tropism compared to a wild-type capsid protein, e.g., a modified capsid protein that is liver-detargeted or has enhanced tropism for nervous system cells. Examples of modified capsid proteins with nervous system cell tropism include, without limitation, U.S. Pat. No. 9,636,370 (e.g., col. 48, lines 54-65; Table 2) and International Publication No. WO 2016/081811 (e.g., at paragraphs [0144] and [0287]), both incorporated by reference herein in their entirety.

In some embodiments, the vector is a self-complementary or duplexed AAV (scAAV) vector. scAAV vectors are described in international patent publication WO 01/92551 (the disclosure of which is incorporated herein by reference in its entirety). Use of scAAV to express the CLN1 ORF may provide an increase in the number of cells transduced, the copy number per transduced cell, or both.

An additional aspect of the invention relates to a transformed cell comprising the polynucleotide, expression cassette, and/or vector of the invention. In some embodiments, the polynucleotide, expression cassette, and/or vector is stably incorporated into the cell genome. The transformed cell may be an in vitro, ex vivo or in vivo cell. In some embodiments, the transformed cell is a cell suitable for production of AAV vectors as described below.

Another aspect of the invention relates to a transgenic animal comprising the polynucleotide, expression cassette, vector, polypeptide, and/or the transformed cell of the invention. In some embodiments, the transgenic animal is a laboratory animal, e.g., a mouse rat, dog, or monkey. In some embodiments, the animal is a model of a disease.

A further aspect of the invention relates to a pharmaceutical formulation comprising the polynucleotide, expression cassette, vector, and/or transformed cell of the invention in a pharmaceutically acceptable carrier as described below.

Methods of Producing Virus Vectors

The present invention further provides methods of producing virus vectors. In one particular embodiment, the present invention provides a method of producing a recombinant AAV particle, comprising providing to a cell permissive for AAV replication: (a) a recombinant AAV template comprising (i) the polynucleotide or expression cassette of the invention, and (ii) an ITR; (b) a polynucleotide comprising Rep coding sequences and Cap coding sequences; under conditions sufficient for the replication and packaging of the recombinant AAV template; whereby recombinant AAV particles are produced in the cell. Conditions sufficient for the replication and packaging of the recombinant AAV template can be, e.g., the presence of AAV sequences sufficient for replication of the AAV template and encapsidation into AAV capsids (e.g., AAV rep sequences and AAV cap sequences) and helper sequences from adenovirus and/or herpesvirus. In particular embodiments, the AAV template comprises two AAV ITR sequences, which are located 5' and 3' to the polynucleotide of the invention, although they need not be directly contiguous thereto.

In some embodiments, the recombinant AAV template comprises an ITR that is not resolved by Rep to make duplexed AAV vectors as described in international patent publication WO 01/92551.

The AAV template and AAV rep and cap sequences are provided under conditions such that virus vector comprising the AAV template packaged within the AAV capsid is produced in the cell. The method can further comprise the step of collecting the virus vector from the cell. The virus vector can be collected from the medium and/or by lysing the cells.

The cell can be a cell that is permissive for AAV viral replication. Any suitable cell known in the art may be employed. In particular embodiments, the cell is a mammalian cell (e.g., a primate or human cell). As another option, the cell can be a trans-complementing packaging cell line that provide functions deleted from a replication-defective helper virus, e.g., 293 cells or other E1a trans-complementing cells.

The AAV replication and capsid sequences may be provided by any method known in the art. Current protocols typically express the AAV rep/cap genes on a single plasmid. The AAV replication and packaging sequences need not be provided together, although it may be convenient to do so. The AAV rep and/or cap sequences may be provided by any viral or non-viral vector. For example, the rep/cap sequences may be provided by a hybrid adenovirus or herpesvirus vector (e.g., inserted into the E1a or E3 regions of a deleted adenovirus vector). EBV vectors may also be employed to express the AAV cap and rep genes. One advantage of this method is that EBV vectors are episomal, yet will maintain a high copy number throughout successive cell divisions (i.e., are stably integrated into the cell as extra-chromosomal elements, designated as an "EBV based nuclear episome," see Margolski, (1992) *Curr. Top. Microbiol. Immun.* 158: 67).

As a further alternative, the rep/cap sequences may be stably incorporated into a cell.

Typically the AAV rep/cap sequences will not be flanked by the TRs, to prevent rescue and/or packaging of these sequences.

The AAV template can be provided to the cell using any method known in the art. For example, the template can be supplied by a non-viral (e.g., plasmid) or viral vector. In particular embodiments, the AAV template is supplied by a herpesvirus or adenovirus vector (e.g., inserted into the E1a or E3 regions of a deleted adenovirus). As another illustration, Palombo et al., (1998) *J. Virology* 72:5025, describes a baculovirus vector carrying a reporter gene flanked by the AAV TRs. EBV vectors may also be employed to deliver the template, as described above with respect to the rep/cap genes.

In another representative embodiment, the AAV template is provided by a replicating rAAV virus. In still other embodiments, an AAV provirus comprising the AAV template is stably integrated into the chromosome of the cell.

To enhance virus titers, helper virus functions (e.g., adenovirus or herpesvirus) that promote a productive AAV infection can be provided to the cell. Helper virus sequences necessary for AAV replication are known in the art. Typically, these sequences will be provided by a helper adenovirus or herpesvirus vector. Alternatively, the adenovirus or herpesvirus sequences can be provided by another non-viral or viral vector, e.g., as a non-infectious adenovirus miniplasmid that carries all of the helper genes that promote efficient AAV production as described by Ferrari et al., (1997) *Nature Med.* 3:1295, and U.S. Pat. Nos. 6,040,183 and 6,093,570.

Further, the helper virus functions may be provided by a packaging cell with the helper sequences embedded in the chromosome or maintained as a stable extrachromosomal element. Generally, the helper virus sequences cannot be packaged into AAV virions, e.g., are not flanked by ITRs.

Those skilled in the art will appreciate that it may be advantageous to provide the AAV replication and capsid sequences and the helper virus sequences (e.g., adenovirus sequences) on a single helper construct. This helper construct may be a non-viral or viral construct. As one nonlimiting illustration, the helper construct can be a hybrid adenovirus or hybrid herpesvirus comprising the AAV rep/cap genes.

In one particular embodiment, the AAV rep/cap sequences and the adenovirus helper sequences are supplied by a single adenovirus helper vector. This vector can further comprise the AAV template. The AAV rep/cap sequences and/or the AAV template can be inserted into a deleted region (e.g., the E1a or E3 regions) of the adenovirus.

In a further embodiment, the AAV rep/cap sequences and the adenovirus helper sequences are supplied by a single adenovirus helper vector. According to this embodiment, the AAV template can be provided as a plasmid template.

In another illustrative embodiment, the AAV rep/cap sequences and adenovirus helper sequences are provided by a single adenovirus helper vector, and the AAV template is integrated into the cell as a provirus. Alternatively, the AAV template is provided by an EBV vector that is maintained within the cell as an extrachromosomal element (e.g., as an EBV based nuclear episome).

In a further exemplary embodiment, the AAV rep/cap sequences and adenovirus helper sequences are provided by a single adenovirus helper. The AAV template can be provided as a separate replicating viral vector. For example, the AAV template can be provided by a AAV particle or a second recombinant adenovirus particle.

According to the foregoing methods, the hybrid adenovirus vector typically comprises the adenovirus 5' and 3' cis sequences sufficient for adenovirus replication and packaging (i.e., the adenovirus terminal repeats and PAC sequence). The AAV rep/cap sequences and, if present, the AAV template are embedded in the adenovirus backbone and are flanked by the 5' and 3' cis sequences, so that these sequences may be packaged into adenovirus capsids. As described above, the adenovirus helper sequences and the AAV rep/cap sequences are generally not flanked by ITRs so that these sequences are not packaged into the AAV virions.

Zhang et al., ((2001) *Gene Ther.* 18:704-12) describe a chimeric helper comprising both adenovirus and the AAV rep and cap genes.

Herpesvirus may also be used as a helper virus in AAV packaging methods. Hybrid herpesviruses encoding the AAV Rep protein(s) may advantageously facilitate scalable AAV vector production schemes. A hybrid herpes simplex virus type I (HSV-1) vector expressing the AAV-2 rep and cap genes has been described (Conway et al., (1999) *Gene Ther.* 6:986 and WO 00/17377.

As a further alternative, the virus vectors of the invention can be produced in insect cells using baculovirus vectors to deliver the rep/cap genes and AAV template as described, for example, by Urabe et al., (2002) *Human Gene Ther.* 13:1935-43.

AAV vector stocks free of contaminating helper virus may be obtained by any method known in the art. For example, AAV and helper virus may be readily differentiated based on size. AAV may also be separated away from helper virus based on affinity for a heparin substrate (Zolotukhin et al. (1999) *Gene Therapy* 6:973). Deleted replication-defective helper viruses can be used so that any contaminating helper virus is not replication competent. As a further alternative, an adenovirus helper lacking late gene expression may be employed, as only adenovirus early gene expression is required to mediate packaging of AAV. Adenovirus mutants defective for late gene expression are known in the art (e.g., ts100K and ts149 adenovirus mutants).

Methods of Using CLN1 Vectors

The present invention also relates to methods for delivering a CLN1 ORF to a cell or a subject to increase production of PPT1, e.g., for therapeutic or research purposes in vitro, ex vivo, or in vivo. Thus, one aspect of the invention relates to a method of expressing a PPT1 polypeptide or a CLN1 open reading frame in a cell, comprising contacting the cell with the polynucleotide, expression cassette, and/or the vector of the invention, thereby expressing the PPT1 polypeptide or the CLN1 open reading frame in the cell. In some embodiments, the cell is an in vitro cell, an ex vivo cell, or an in vivo cell.

Another aspect of the invention relates to a method of expressing a PPT1 polypeptide or a CLN1 open reading frame in a subject, comprising delivering to the subject the polynucleotide, expression cassette, vector, and/or transformed cell of the invention, thereby expressing the PPT1 polypeptide or the CLN1 open reading frame in the subject. In some embodiments, the subject is an animal model of neuronal ceroid lipofuscinosis or other disorder associated with aberrant CLN1 gene expression.

A further aspect of the invention relates to a method of treating a disorder associated with aberrant expression of a CLN1 gene or aberrant activity of a CLN1 gene product in a subject in need thereof, comprising delivering to the subject a therapeutically effective amount of the polynucleotide, expression cassette, vector, and/or transformed cell of the invention, thereby treating the disorder associated with aberrant expression of the CLN1 gene in the subject. In some embodiments, the disorder associated with expression of the CLN1 gene is infantile neuronal ceroid lipofuscinosis or a later onset form of neuronal ceroid lipofuscinosis that includes but is not limited to late-infantile, juvenile, or adult-onset neuronal ceroid lipofuscinosis.

In certain embodiments, the polynucleotide, expression cassette, vector, and/or transformed cell is delivered to the nervous system of the subject, e.g., directly to the nervous system of the subject. In some embodiments, the polynucleotide, expression cassette, vector, and/or transformed cell is delivered by intrathecal, intracerebral, intraventricular, intranasal, intra-aural, intra-ocular, or peri-ocular delivery, or any combination thereof. In some embodiments, the polynucleotide, expression cassette, vector, and/or transformed cell is delivered intravenously. In another embodiment, the polynucleotide, expression cassette, and/or vector is delivered by injection, electroporation, gene gun, sonoporation, magnetofection, hydrodynamic delivery, or other physical or chemical methods.

Recombinant virus vectors according to the present invention find use in both veterinary and medical applications. Suitable subjects include both avians and mammals. The term "avian" as used herein includes, but is not limited to, chickens, ducks, geese, quail, turkeys, pheasant, parrots, parakeets. The term "mammal" as used herein includes, but is not limited to, humans, primates non-human primates (e.g., monkeys and baboons), cattle, sheep, goats, pigs, horses, cats, dogs, rabbits, rodents (e.g., rats, mice, hamsters, and the like), etc. Human subjects include neonates, infants, juveniles, and adults. Optionally, the subject is "in need of" the methods of the present invention, e.g., because the subject has or is believed at risk for a disorder including those described herein or that would benefit from the delivery of a polynucleotide including those described herein. As a further option, the subject can be a laboratory animal and/or an animal model of disease.

In certain embodiments, the polynucleotide of the invention is administered to a subject in need thereof as early as possible in the life of the subject, e.g., as soon as the subject is diagnosed with aberrant CLN1 expression and/or aberrant PPT1 activity. In some embodiments, the polynucleotide is administered to a newborn subject, e.g., after newborn screening has identified aberrant CLN1 expression and/or aberrant PPT1 activity. In some embodiments, the polynucleotide is administered to a fetus in utero, e.g., after prenatal screening has identified aberrant CLN1 expression and/or aberrant PPT1 activity. In some embodiments, the polynucleotide is administered to a subject as soon as the subject develops symptoms associated with aberrant CLN1 expression and/or aberrant PPT1 activity or is suspected or diagnosed as having aberrant CLN1 expression and/or aberrant PPT1 activity. In some embodiments, the polynucleotide is administered to a subject before the subject develops symptoms associated with aberrant CLN1 expression and/or aberrant PPT1 activity, e.g., a subject that is suspected or diagnosed as having aberrant CLN1 expression and/or aberrant PPT1 activity but has not started to exhibit symptoms.

In particular embodiments, the present invention provides a pharmaceutical composition or a pharmaceutical formulation comprising a virus vector of the invention in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and will preferably be in solid or liquid particulate form.

By "pharmaceutically acceptable" it is meant a material that is not toxic or otherwise undesirable, i.e., the material may be administered to a subject without causing any undesirable biological effects.

One aspect of the present invention is a method of transferring a polynucleotide encoding a PPT1 polypeptide or a CLN1 ORF to a cell in vitro. The virus vector may be introduced to the cells at the appropriate multiplicity of infection according to standard transduction methods appropriate for the particular target cells. Titers of the virus vector or capsid to administer can vary, depending upon the target cell type and number, and the particular virus vector or capsid, and can be determined by those of skill in the art without undue experimentation. In particular embodiments, at least about $10^3$ infectious units, more preferably at least about $10^5$ infectious units are introduced to the cell.

The cell(s) into which the vector (e.g., viral or non-viral vector) can be introduced may be of any type, including but not limited to neural cells (including cells of the peripheral and central nervous systems, in particular, brain cells such as neurons, oligodendrocytes, glial cells, astrocytes), lung cells, cells of the eye (including retinal cells, retinal pigment epithelium, and corneal cells), epithelial cells (e.g., gut and respiratory epithelial cells), skeletal muscle cells (including myoblasts, myotubes and myofibers), diaphragm muscle cells, dendritic cells, pancreatic cells (including islet cells), hepatic cells, a cell of the gastrointestinal tract (including smooth muscle cells, epithelial cells), heart cells (including cardiomyocytes), bone cells (e.g., bone marrow stem cells), hematopoietic stem cells, spleen cells, keratinocytes, fibroblasts, endothelial cells, prostate cells, joint cells (including, e.g., cartilage, meniscus, synovium and bone marrow), germ cells, and the like. Alternatively, the cell may be any progenitor cell. As a further alternative, the cell can be a stem cell (e.g., neural stem cell, liver stem cell). As still a further alternative, the cell may be a cancer or tumor cell (cancers and tumors are described above). Moreover, the cells can be from any species of origin, as indicated above.

The viral or non-viral vectors may be introduced to cells in vitro for the purpose of administering the modified cell to a subject. In particular embodiments, the cells have been removed from a subject, the vector is introduced therein, and the cells are then replaced back into the subject. Methods of removing cells from subject for treatment ex vivo, followed by introduction back into the subject are known in the art (see, e.g., U.S. Pat. No. 5,399,346). Alternatively, a recombinant virus vector is introduced into cells from another subject, into cultured cells, or into cells from any other suitable source, and the cells are administered to a subject in need thereof.

Suitable cells for ex vivo gene therapy are as described above. Dosages of the cells to administer to a subject will vary upon the age, condition and species of the subject, the type of cell, the nucleic acid being expressed by the cell, the mode of administration, and the like. Typically, at least about $10^2$ to about $10^8$ or about $10^3$ to about $10^6$ cells will be administered per dose in a pharmaceutically acceptable carrier. In particular embodiments, the cells transduced with the virus vector are administered to the subject in an effective amount in combination with a pharmaceutical carrier.

A further aspect of the invention is a method of administering the virus vectors of the invention to a subject. In particular embodiments, the method comprises a method of delivering a polynucleotide encoding a PPT1 polypeptide or a fragment thereof or a CLN1 ORF to an animal subject, the method comprising: administering an effective amount of a virus vector according to the invention to an animal subject. Administration of the virus vectors of the present invention to a human subject or an animal in need thereof can be by any means known in the art. Optionally, the virus vector is delivered in an effective dose in a pharmaceutically acceptable carrier.

Dosages of the virus vectors to be administered to a subject will depend upon the mode of administration, the disease or condition to be treated, the individual subject's condition, the particular virus vector, and the nucleic acid to be delivered, and can be determined in a routine manner. Exemplary doses for achieving therapeutic effects are virus titers of at least about $10^5$, $10^6$, $10^7$, $10^8$, $10^9$, $10^{10}$, $10^{11}$, $10^{12}$, $10^3$, $10^{14}$, $10^{15}$, $10^{16}$, $10^{17}$, or $10^{18}$ transducing units or more, e.g., about $10^7$, $10^8$, $10^9$, $10^{10}$, $10^{11}$, $10^{12}$, $10^{13}$, $10^{14}$, $10^{15}$, or $10^{16}$ transducing units, e.g., about $10^{12}$ to about $10^{14}$ transducing units.

In particular embodiments, more than one administration (e.g., two, three, four or more administrations) may be employed to achieve the desired level of gene expression over a period of various intervals, e.g., hourly, daily, weekly, monthly, yearly, etc. Each administration may be by the same or different routes, e.g., two administrations 1 hour apart by different routes.

Exemplary modes of administration include oral, rectal, transmucosal, topical, intranasal, inhalation (e.g., via an aerosol), buccal (e.g., sublingual), vaginal, intrathecal, intraocular, transdermal, in utero (or in ovo), parenteral (e.g., intravenous, subcutaneous, intradermal, intramuscular [including administration to skeletal, diaphragm and/or cardiac muscle], intradermal, intrapleural, intracerebral, and intraarticular), topical (e.g., to both skin and mucosal surfaces, including airway surfaces, and transdermal administration), intro-lymphatic, and the like, as well as direct tissue or organ injection (e.g., to liver, skeletal muscle, cardiac muscle, diaphragm muscle or brain). Administration can also be to a tumor (e.g., in or a near a tumor or a lymph node). The most suitable route in any given case will depend on the nature and severity of the condition being treated and on the nature of the particular vector that is being used.

In some embodiments, the viral vector is administered to the CNS, the peripheral nervous system, or both.

In some embodiments, the viral vector is administered directly to the CNS, e.g., the brain or the spinal cord. Direct administration can result in high specificity of transduction of CNS cells, e.g., wherein at least 80%, 85%, 90%, 95% or more of the transduced cells are CNS cells. Any method known in the art to administer vectors directly to the CNS can be used. The vector may be introduced into the spinal cord, brainstem (medulla oblongata, pons), midbrain (hypothalamus, thalamus, epithalamus, pituitary gland, substantia nigra, pineal gland), cerebellum, telencephalon (corpus striatum, cerebrum including the occipital, temporal, parietal and frontal lobes, cortex, basal ganglia, hippocampus and amygdala), limbic system, neocortex, corpus striatum, cerebrum, and inferior colliculus. The vector may also be administered to different regions of the eye such as the retina, cornea or optic nerve. The vector may be delivered into the cerebrospinal fluid (e.g., by lumbar puncture) for more disperse administration of the vector.

The delivery vector may be administered to the desired region(s) of the CNS by any route known in the art, including but not limited to, intrathecal, intracerebral, intraventricular, intranasal, intra-aural, intra-ocular (e.g., intravitreous, sub-retinal, anterior chamber) and peri-ocular (e.g., sub-Tenon's region) delivery or any combination thereof.

The delivery vector may be administered in a manner that produces a more widespread, diffuse transduction of tissues, including the CNS, the peripheral nervous system, and/or other tissues.

Typically, the viral vector will be administered in a liquid formulation by direct injection (e.g., stereotactic injection) to the desired region or compartment in the CNS and/or other tissues. In some embodiments, the vector can be delivered via a reservoir and/or pump. In other embodiments, the vector may be provided by topical application to the desired region or by intra-nasal administration of an aerosol formulation. Administration to the eye or into the ear, may be by topical application of liquid droplets. As a further alternative, the vector may be administered as a solid, slow-release formulation. Controlled release of parvovirus and AAV vectors is described by international patent publication WO 01/91803.

Injectables can be prepared in conventional forms, either as liquid solutions or suspensions, solid forms suitable for solution or suspension in liquid prior to injection, or as emulsions. Alternatively, one may administer the virus vector in a local rather than systemic manner, for example, in a depot or sustained-release formulation. Further, the virus vector can be delivered dried to a surgically implantable matrix such as a bone graft substitute, a suture, a stent, and the like (e.g., as described in U.S. Pat. No. 7,201,898).

The term "pharmaceutical composition" refers to any dosage form, which includes but is not limited to tablets, coated tablet, powder, powder for reconstitution, pellets, beads, mini-tablets, multilayer tablet, bilayered tablet, tablet-in-tablet, pills, micro-pellets, small tablet units, MUPS (multiple unit pellet system), disintegrating tablets, dispersible tablets, granules, microspheres, multiparticulates, capsule (filled with powder, powder for reconstitution, pellets, beads, mini-tablets, pills, micro-pellets, small tablet units, MUPS, orally disintegrating MUPS, disintegrating tablets, dispersible tablets, granules, sprinkles, microspheres and multiparticulates), sachets (filled with powders, powders for reconstitution, pellets, beads, mini-tablets, pills, micro-pellets, small tablet units, MUDS, disintegrating tablets, dispersible tablets, modified release tablets or capsules, effervescent granules, granules, sprinkles, microspheres and multiparticulates), or sprinkles. Pharmaceutical compositions suitable for oral administration can be presented in discrete units, such as capsules, cachets, lozenges, or tablets, each containing a predetermined amount of the composition of this invention; as a powder or granules; as a solution or a suspension in an aqueous or non-aqueous liquid; or as an oil-in-water or water-in-oil emulsion. Oral delivery can be performed by complexing a virus vector of the present invention to a carrier capable of withstanding degradation by digestive enzymes in the gut of an animal. Examples of such carriers include plastic capsules or tablets, as known in the art. Such formulations are prepared by any suitable method of pharmacy, which includes the step of bringing into association the composition and a suitable carrier (which may contain one or more accessory ingredients as noted above). In general, the pharmaceutical composition according to embodiments of the present invention are prepared by uniformly and intimately admixing the composition with a liquid or finely divided solid carrier, or both, and then, if necessary, shaping the resulting mixture. For example, a tablet can be prepared by compressing or molding a powder or granules containing the composition, optionally with one or more accessory ingredients. Compressed tablets are prepared by compressing, in a suitable machine, the composition in a free-flowing form, such as a powder or granules optionally mixed with a binder, lubricant, inert diluent, and/or surface active/dispersing agent(s). Molded tablets are made by molding, in a suitable machine, the powdered compound moistened with an inert liquid binder. In one embodiment, a pharmaceutical composition comprises a pharmaceutical formulation which refers to a mixture or solution containing a therapeutically effective amount of an active pharmaceutical ingredient. The active pharmaceutical ingredients include but are not limited to a chemical, a polypeptide, a nucleotide, an antibody, or a lipid.

Pharmaceutical compositions suitable for buccal (sublingual) administration include lozenges comprising the composition of this invention in a flavored base, usually sucrose and acacia or tragacanth; and pastilles comprising the composition in an inert base such as gelatin and glycerin or sucrose and acacia.

Pharmaceutical compositions suitable for parenteral administration can comprise sterile aqueous and non-aqueous injection solutions of the composition of this invention, which preparations are optionally isotonic with the blood of the intended recipient. These preparations can contain antioxidants, buffers, bacteriostats and solutes, which render the composition isotonic with the blood of the intended recipient. Aqueous and non-aqueous sterile suspensions, solutions and emulsions can include suspending agents and thickening agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The compositions can be presented in unit/dose or multidose containers, for example, in sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, an injectable, stable, sterile composition of this invention in a unit dosage form in a sealed container can be provided. The composition can be provided in the form of a lyophilizate, which can be reconstituted with a suitable pharmaceutically acceptable carrier to form a liquid composition suitable for injection into a subject. The unit dosage form can be from about 1 µg to about 10 grams of the composition of this invention. When the composition is substantially water-insoluble, a sufficient amount of emulsifying agent, which is physiologically acceptable, can be included in sufficient quantity to emulsify the composition in an aqueous carrier. One such useful emulsifying agent is phosphatidyl choline.

Pharmaceutical compositions suitable for rectal administration can be presented as unit dose suppositories. These can be prepared by admixing the composition with one or more conventional solid carriers, such as for example, cocoa butter and then shaping the resulting mixture.

Pharmaceutical compositions of this invention suitable for topical application to the skin can take the form of an ointment, cream, lotion, paste, gel, spray, aerosol, or oil. Carriers that can be used include, but are not limited to, petroleum jelly, lanoline, polyethylene glycols, alcohols, transdermal enhancers, and combinations of two or more thereof. In some embodiments, for example, topical delivery can be performed by mixing a pharmaceutical composition of the present invention with a lipophilic reagent (e.g., DMSO) that is capable of passing into the skin.

Pharmaceutical compositions suitable for transdermal administration can be in the form of discrete patches adapted to remain in intimate contact with the epidermis of the subject for a prolonged period of time. Compositions suitable for transdermal administration can also be delivered by iontophoresis (see, for example, *Pharm. Res.* 3:318 (1986)) and typically take the form of an optionally buffered aqueous solution of the composition of this invention. Suitable formulations can comprise citrate or bis\tris buffer (pH 6) or ethanol/water and can contain from 0.1 to 0.2M active ingredient.

The virus vectors disclosed herein may be administered to the lungs of a subject by any suitable means, for example, by administering an aerosol suspension of respirable particles comprised of the virus vectors, which the subject inhales. The respirable particles may be liquid or solid. Aerosols of liquid particles comprising the virus vectors may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the virus vectors may likewise be produced with any solid particulate medicament aerosol generator, by techniques known in the pharmaceutical art.

Having described the present invention, the same will be explained in greater detail in the following examples, which are included herein for illustration purposes only, and which are not intended to be limiting to the invention.

Example 1

AAV Vectors Comprising Optimized CLN1

An AAV vector genome cassette was developed to express a CLN1 ORF. This cassette was designed to provide maximal expression from a self-complementary AAV genome that would be packaged within multiple AAV capsids. The cassette consists of, in order: mutant AAV2 ITR, CMV enhancer, chicken beta actin promoter, hybrid/modified MVM intron, codon optimized human CLN1 ORF, bovine growth hormone polyadenylation site, and wild-type (WT) AAV2 ITR (FIG. 1). The expression of CLN1 was verified by transfecting the expression cassette into HEK293 cells and the expressed protein was detected in the cells and media by Western blot.

Figure 2:
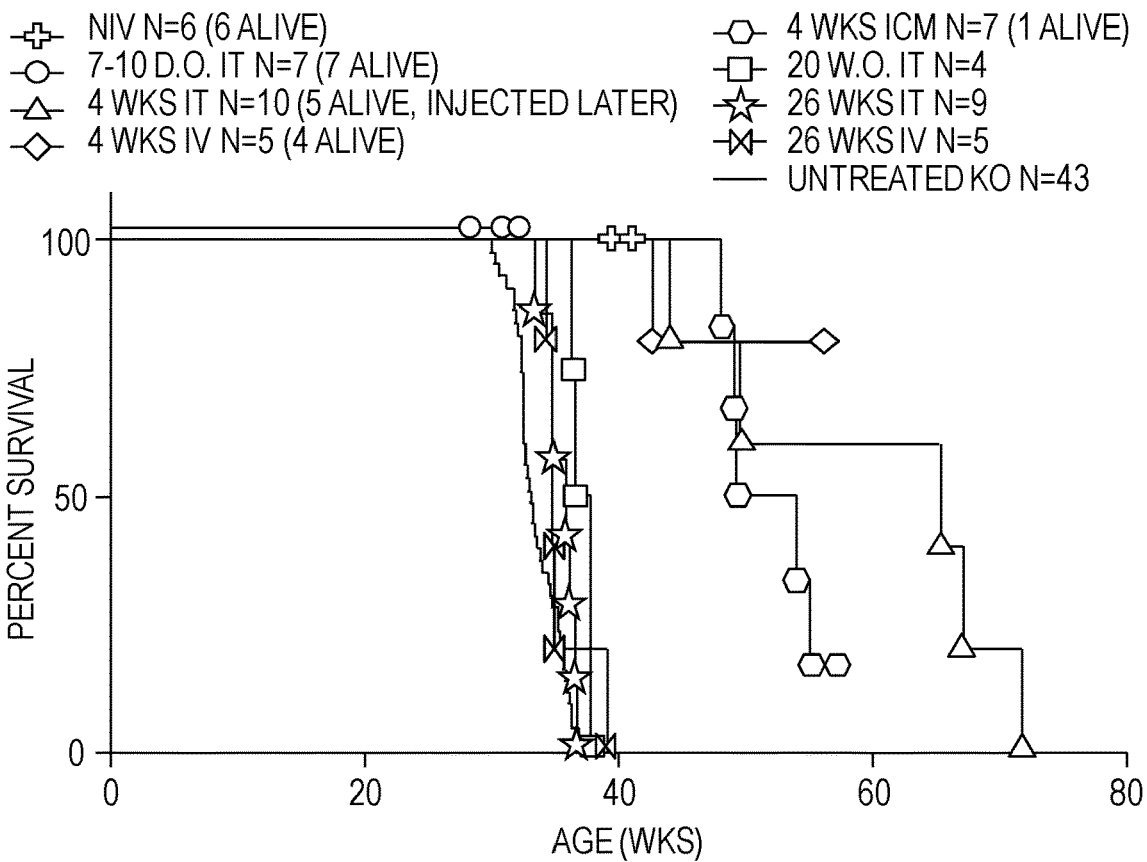
FIG. 2 shows survival curves for all cohorts of CLN1 knockout mice treated with the CLN1 AAV vector of the invention. MV=neonatal IV; IT=lumbar intrathecal injection; IV=intravenous injection; ICM=cisterna magna injection; d.o.=day old; w.o.=week old; KO=knock-out. Ages are the age at which they are injected. "Deaths" are scored by a 20% decrease in weight or significant morbidity requiring euthanasia.
Figure 3:
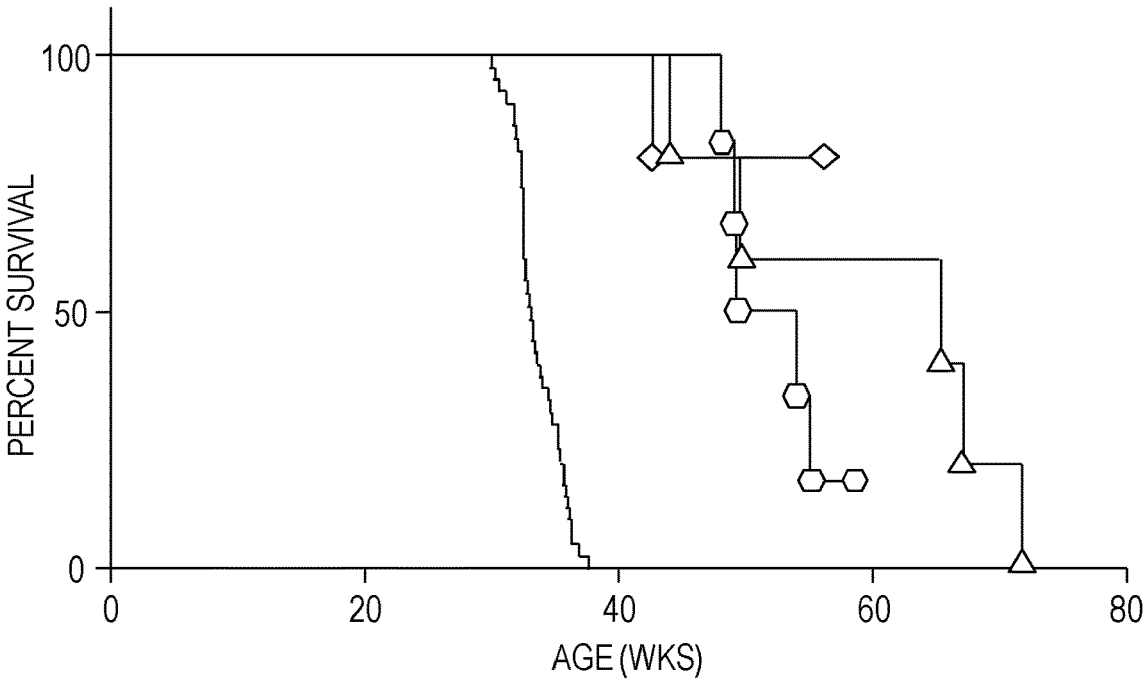
FIG. 3 shows survival curves for cohorts of CLN1 knockout mice treated with the CLN1 AAV vector of the invention at 4 weeks of age.
Figure 4:
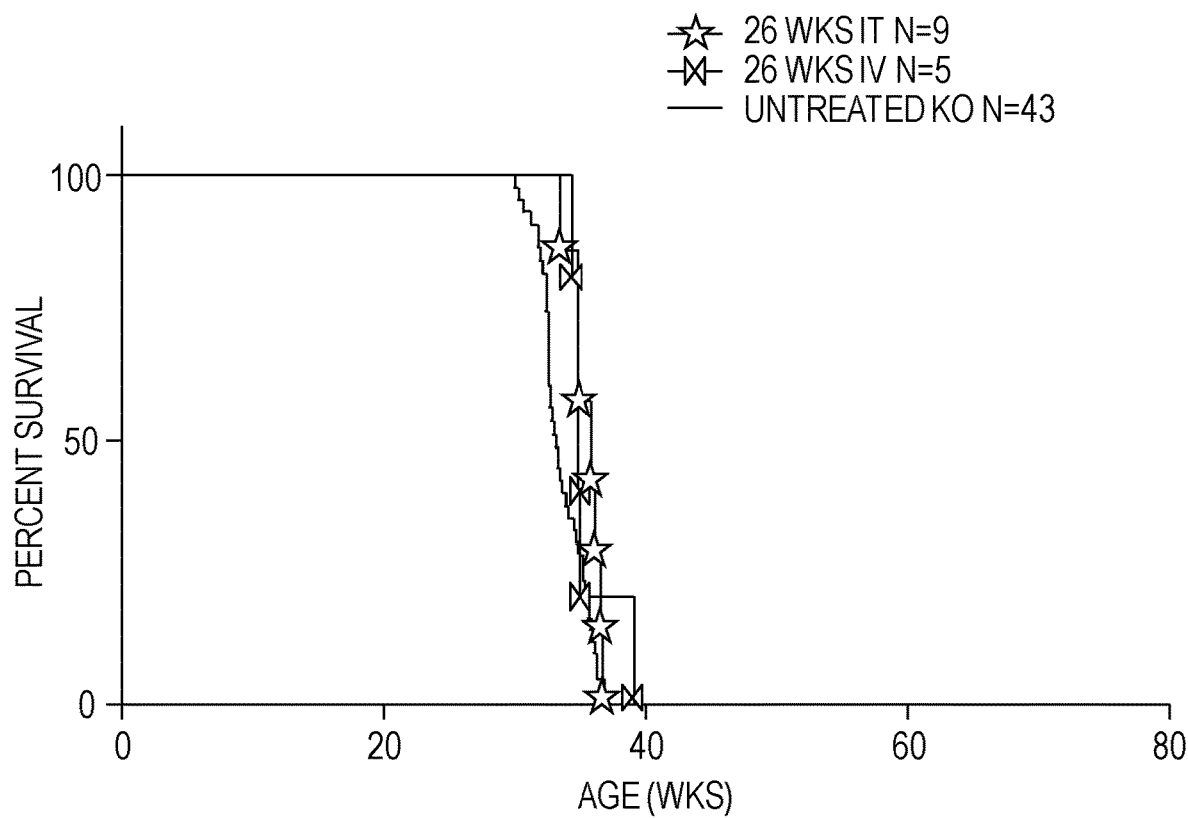
FIG. 4 shows survival curves for cohorts of CLN1 knockout mice treated with the CLN1 AAV vector of the invention at 26 weeks of age.
Figure 5:
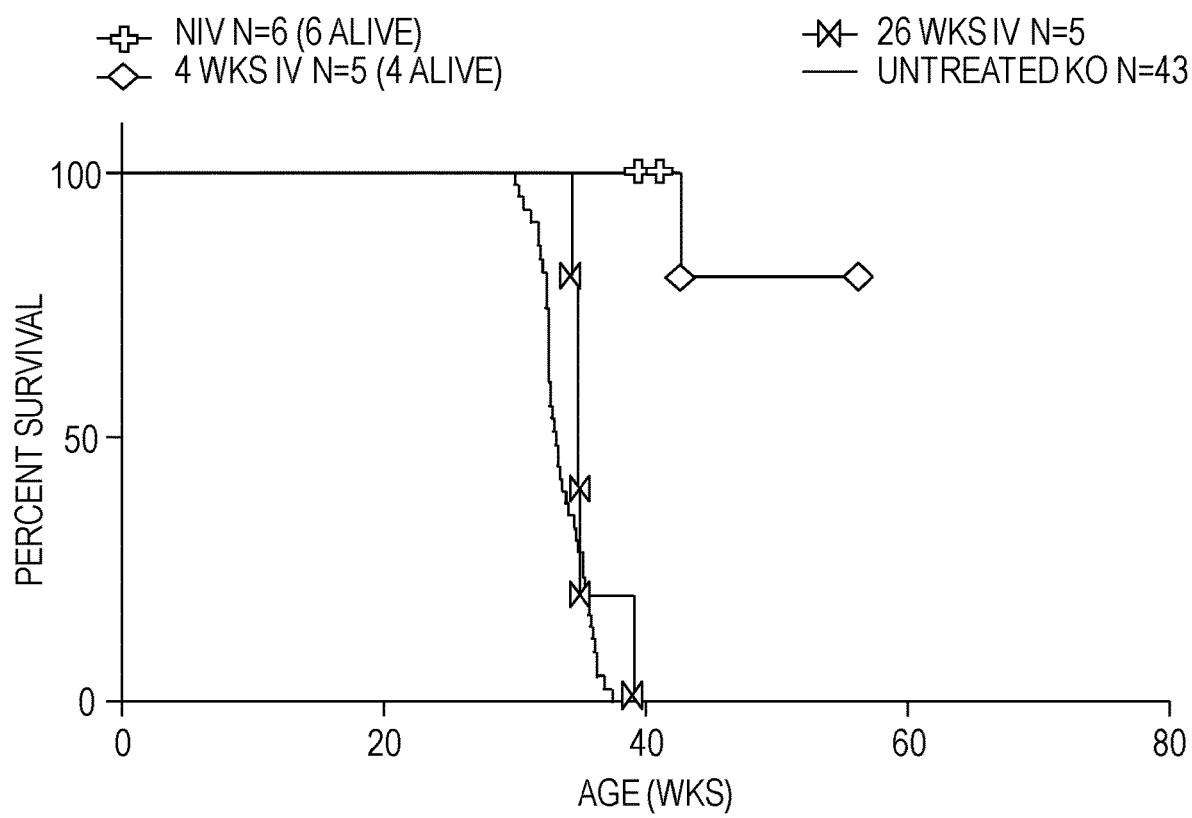
FIG. 5 shows survival curves for intravenous cohorts of CLN1 knockout mice treated with the CLN1 AAV vector of the invention.
Figure 6:
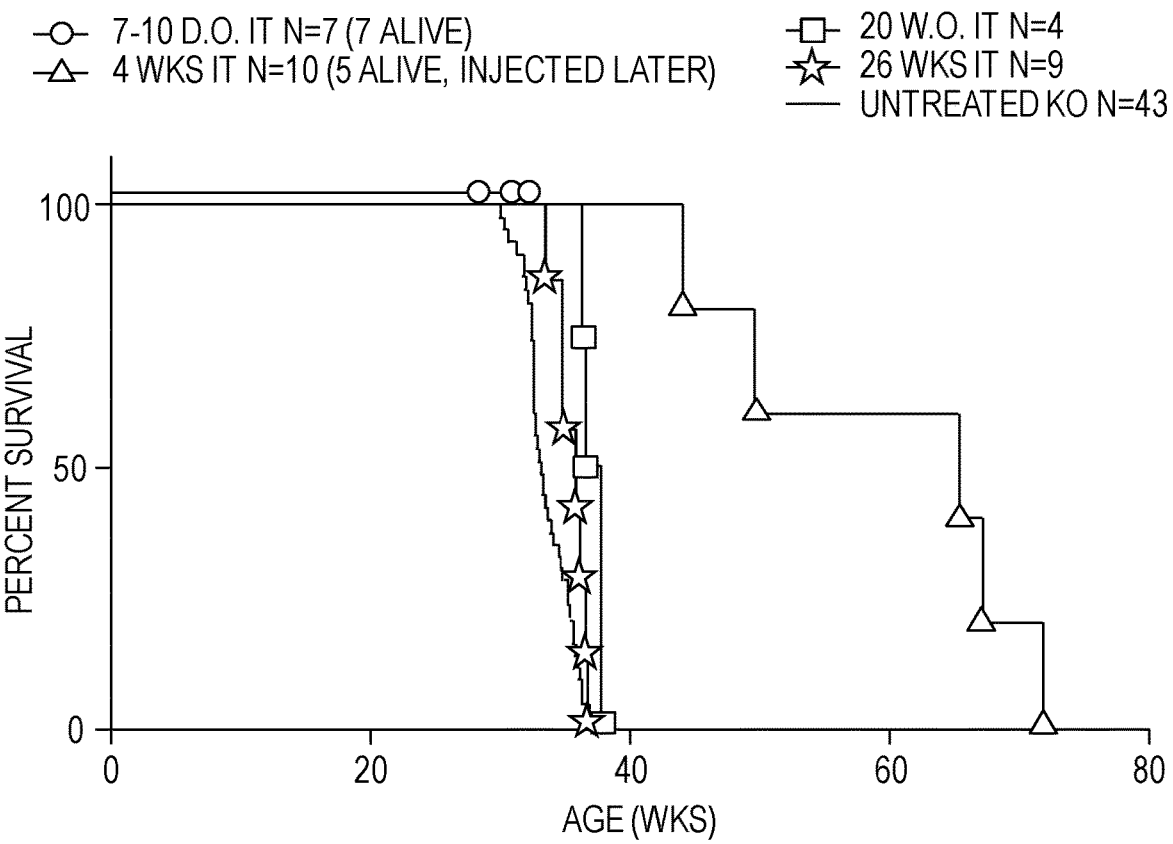
FIG. 6 shows survival curves for intrathecal cohorts of CLN1 knockout mice treated with the CLN1 AAV vector of the invention.

The CLN1 expression cassette was packaged within an AAV9 capsid and the resulting vector was used to dose CLN1 knockout mice intrathecally, intravenously, or by cisterna magna injection. A wild-type AAV9 capsid was used for intrathecal injection and a liver-detargeted AAV9 capsid (AAV9.47) was used for intravenous injection. The AAV9 vector was administered intrathecally at doses of $7\times10^{10}$, $2.2\times10^{11}$, or $7\times10^{11}$ vector genomes, or at birth intravenously at a dose of $2.8\times10^{11}$ vector genomes. The AAV9.47 vector was administered at a dose of $1\times10^{12}$ vector genomes. Vectors were administered at birth, 7-10 days, 4 weeks, 20 weeks, or 26 weeks. Results are shown in FIG. 2 for all cohorts and in FIGS. 3-6 for different cohorts.

These studies showed that when $7\times10^{10}$ vg of scAAV9/CLN1 was administered intrathecally, the lifespan of the mice doubled from 8 months to 16 months. The vector was also found to be therapeutic when administered intravenously.

Figure 7A:
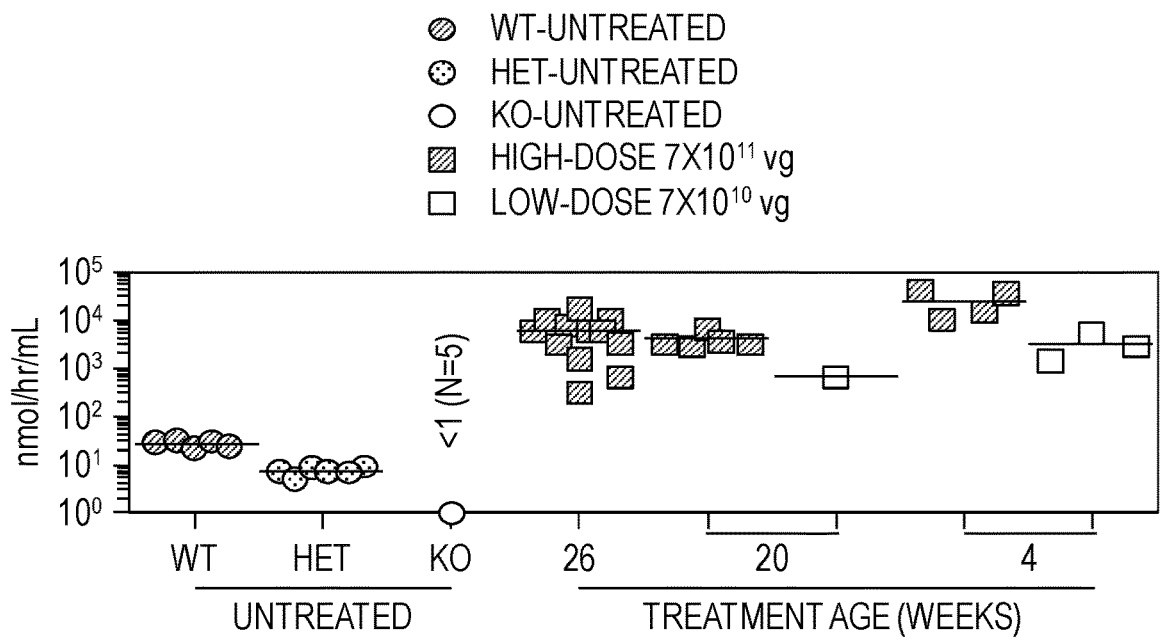
FIGS. 7A-7B show scAAV9/CLN1 therapy increases serum PPT1 levels and recues survival. A. CLN1 mice were given therapy i.t. at the indicated ages and serum was taken after 3 months or at the humane endpoint. Data are reported as nmol substrate processed per hr per mL serum. Untreated KO mice fall off scale (values <1) so are not shown. B. Kaplan-Meier plots comparing mice treated with low-dose therapy (top panel) and high-dose therapy (bottom panel) at different ages. Untreated KO mice are shown in both panels as a reference.
Figure 7B:
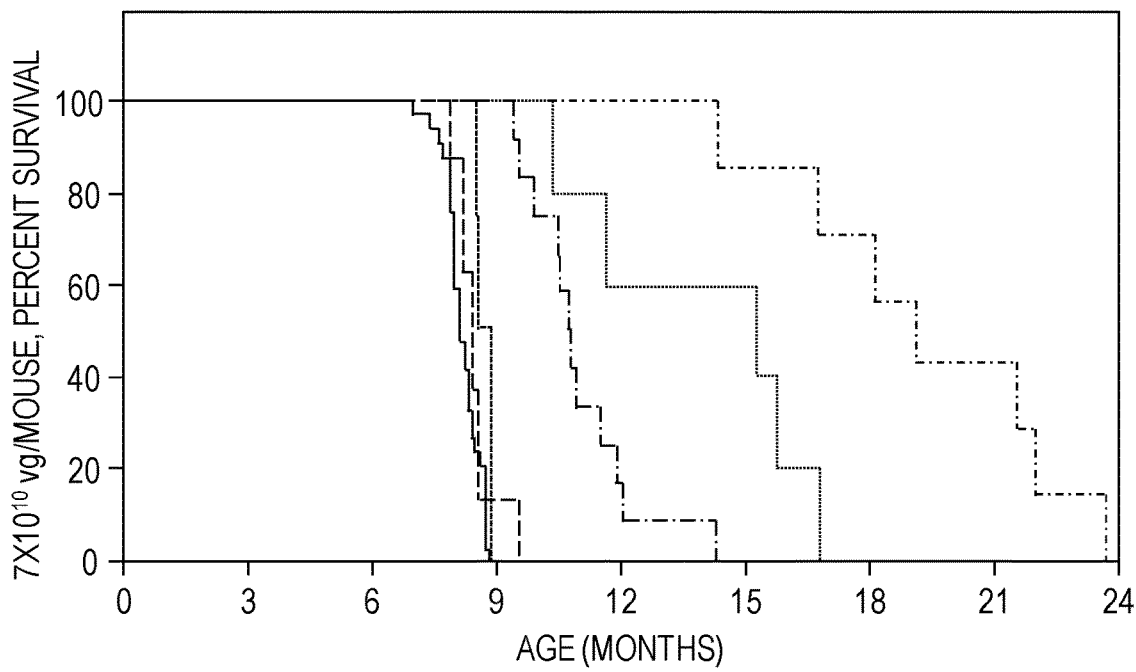
Figure 7B:
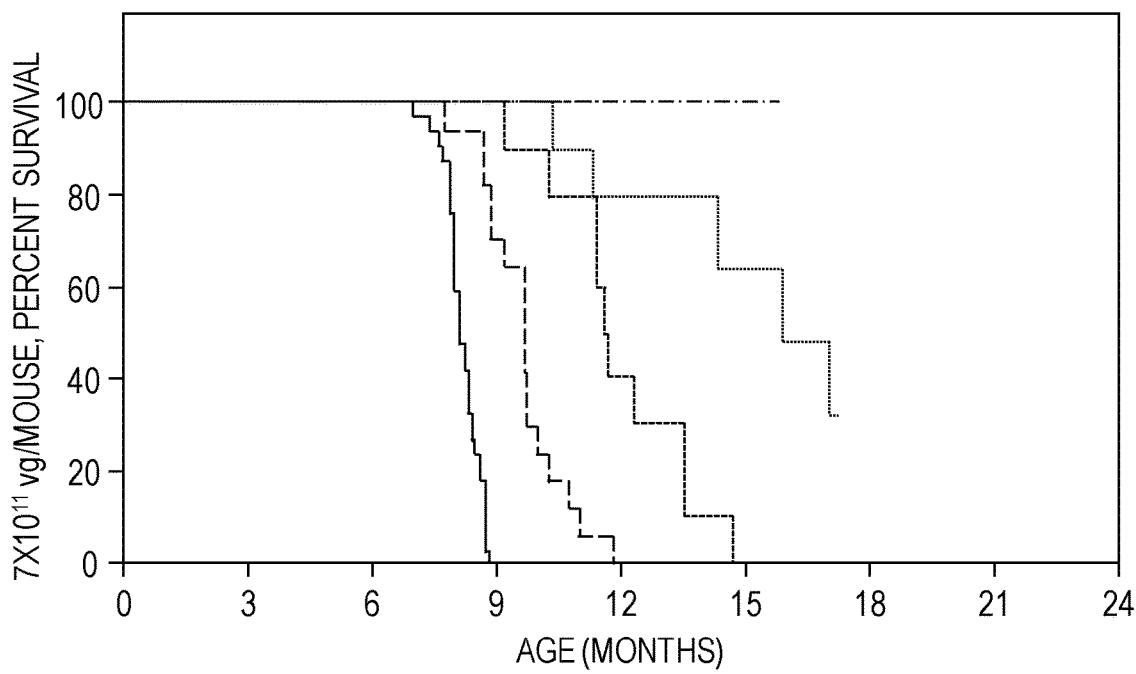

FIG. 7A shows an increase in serum PPT1 levels in mice administered scAAV9/CLN1 therapy. The vector was injected intrathecally into wild-type, heterologous and CLN1 knockout mice at doses of $7\times10^{10}$ and $7\times10^{11}$ vg at 4, 20, and 26 weeks of age. Serum PPT1 levels were measured 3 months after administration or at the humane endpoint. Supraphysiological PPT1 levels were observed at all time points and dosages. FIG. 7B shows survival curves for groups of mice administered scAAV9/CLN1 at different ages at doses of $7\times10^{10}$ and $7\times10^{11}$ vg. Survival rates increased with earlier administration at both doses.

Behavioral assays were performed on treated mice to detect improvements in behavior after vector administration.

Figure 8A:
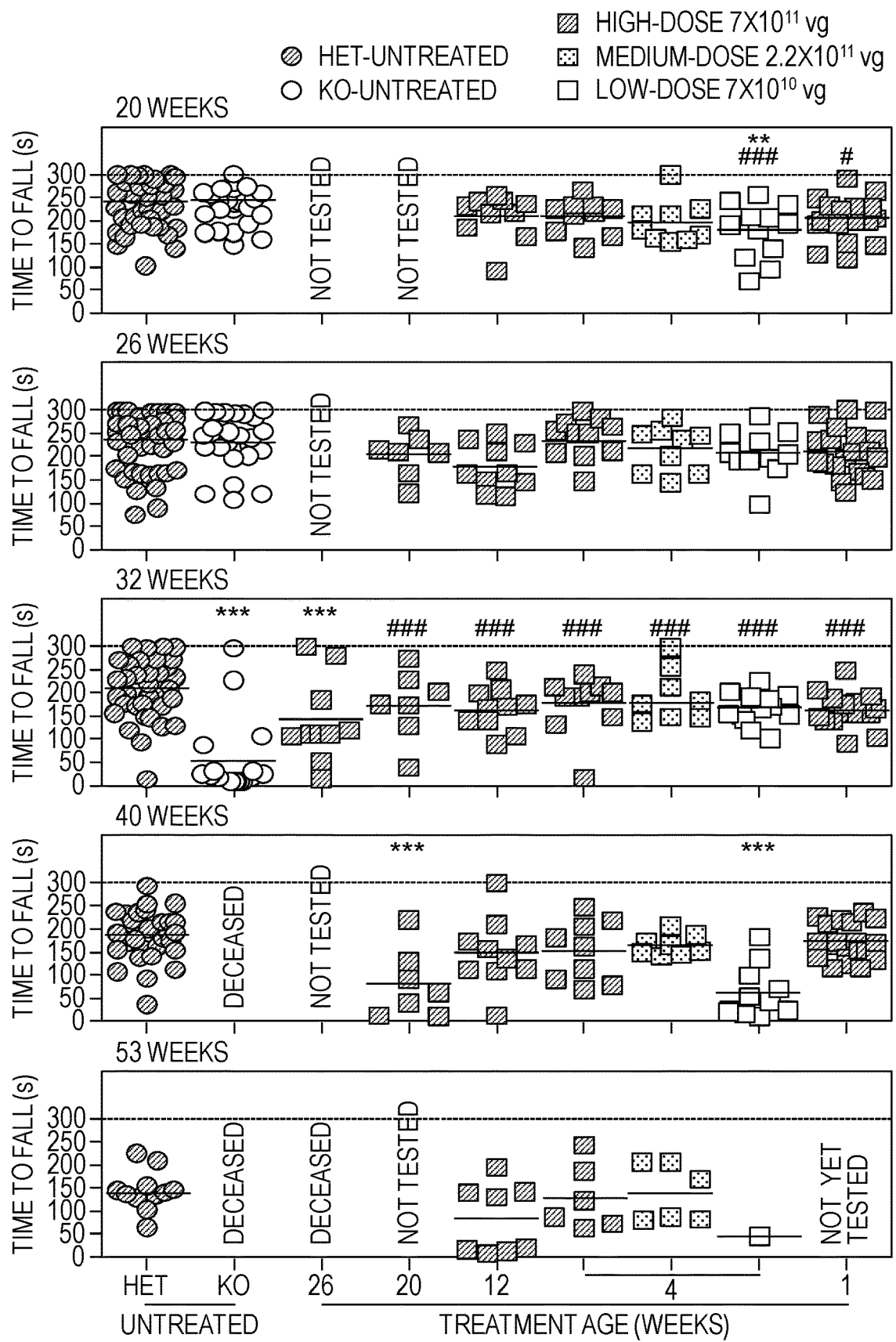
FIGS. 8A-8B show accelerating Rotarod performance. Each point represents the average latency to fall for a given mouse across two-trials at a given testing age. A. Cohorts whose behavioral testing began at <1 yr of age. B. Cohort whose behavioral testing began at >1 yr of age. A one-way ANOVA with Tukey's post-hoc multiple comparison was used to assess differences in group means as compared to untreated HETs (*) or untreated KOs (#): */#p<0.05, /##p<0.01, */###p<0.001.
Figure 8B:
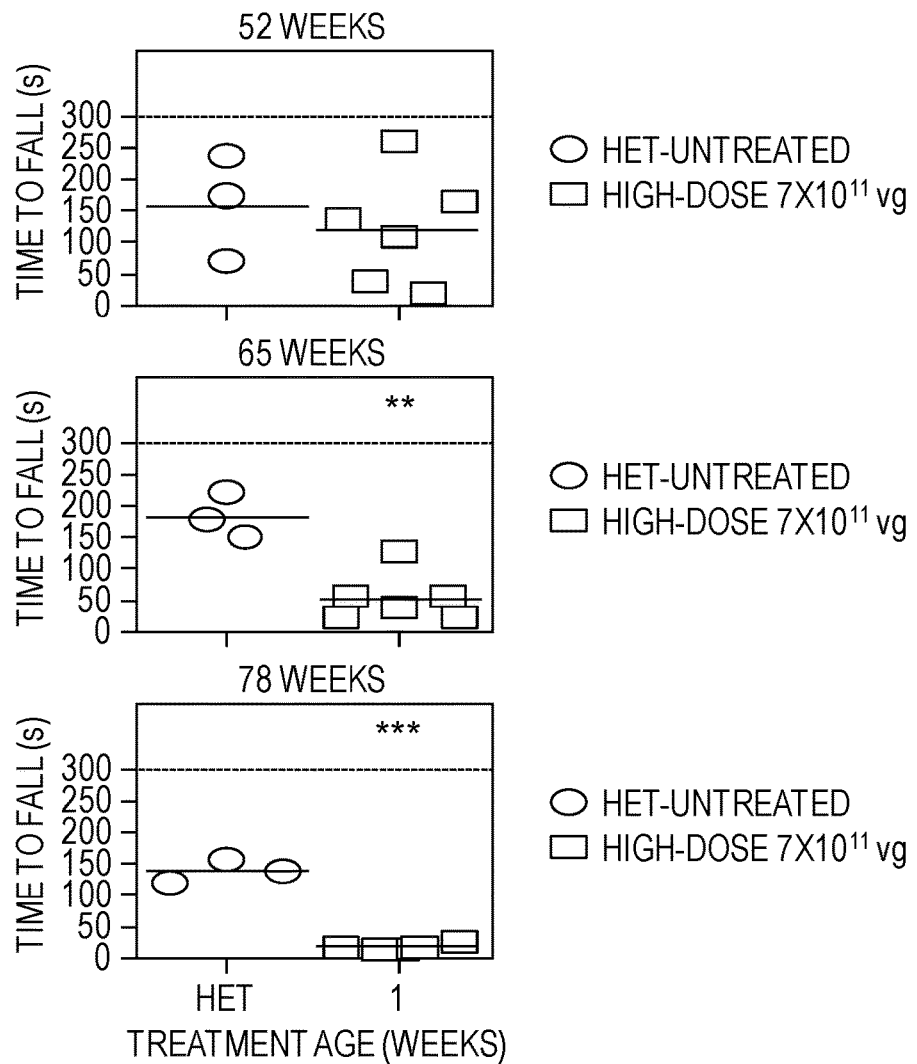

In a test for motor coordination, mice (heterologous untreated, knockout untreated, knockout treated with low ($7\times10^{10}$ vg), medium ($2.2\times10^{11}$ vg), or high dose ($7\times10^{11}$ vg) at different ages) were placed on the top of a rotarod with an initial speed of 3 rpm. The speed was progressively increased to 30 rpm throughout the course of a 300 sec trial. Latency to fall from the top of the rod was measured. Tests were carried out at different ages. Results are shown in FIG. 8A (behavioral testing began at <1 year of age) and FIG. 8B (behavioral testing began at >1 year of age). Gene transfer of the CLN1 expression cassette via an AAV vector provided some benefit in motor function to knockout mice, at all doses and ages of treatment shown, with earlier intervention at a higher dose providing the greatest benefit.

Figure 9B:
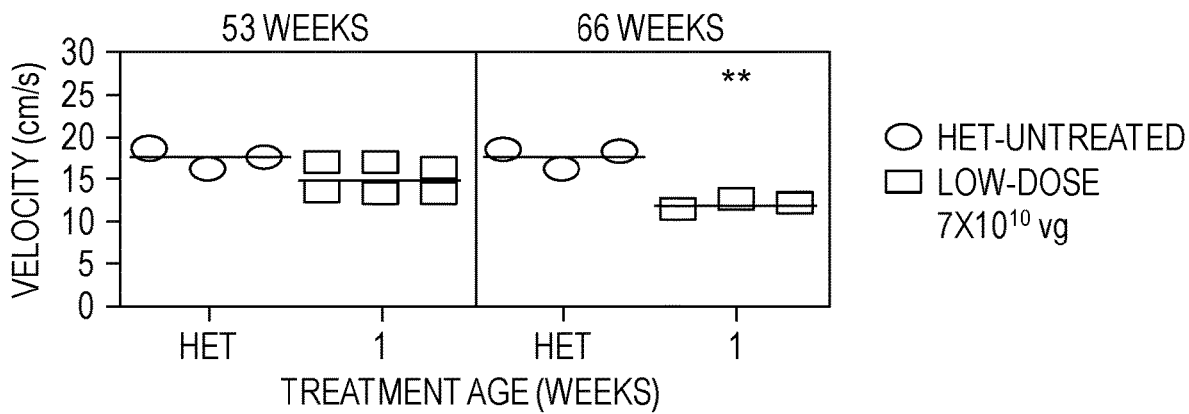
FIGS. 9A-9B show swim speed assessment in the Morris Water Maze. Each point represents the swim speed for a given mouse at the tested age averaged across 2-3 days with 4 trials per day. A. Cohorts whose behavioral testing began at <1 yr of age. A one-way ANOVA with Tukey's post-hoc multiple comparison was used to assess differences in group means as compared to untreated HETs (*) or untreated KOs (#): */#p<0.05, /##p<0.01, */###p<0.001. B. Cohort whose behavioral testing began at >1 yr of age. Differences in group means were determined by the unpaired Student's t test: **p<0.01.
Figure 9A:
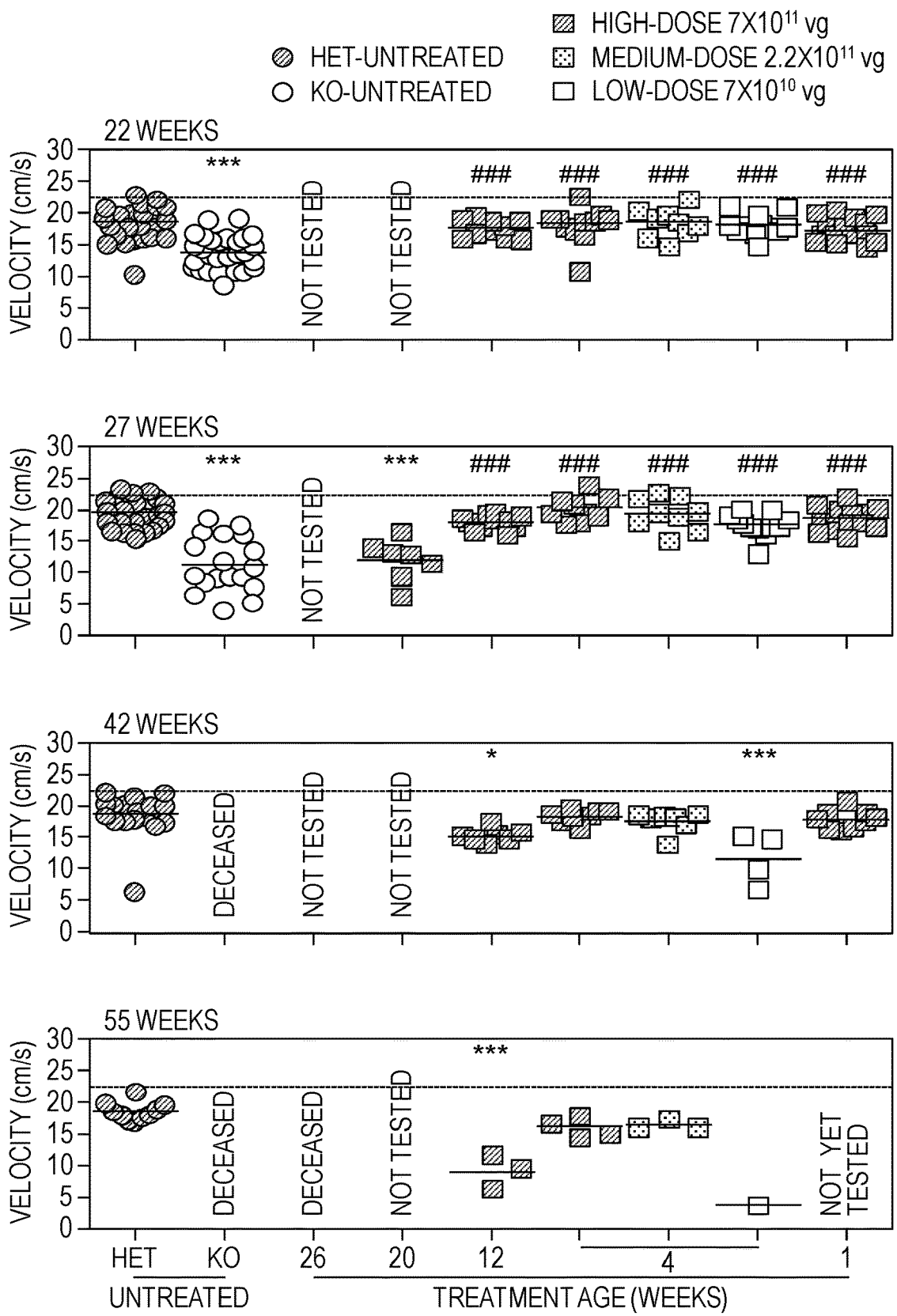
Figure 10A:
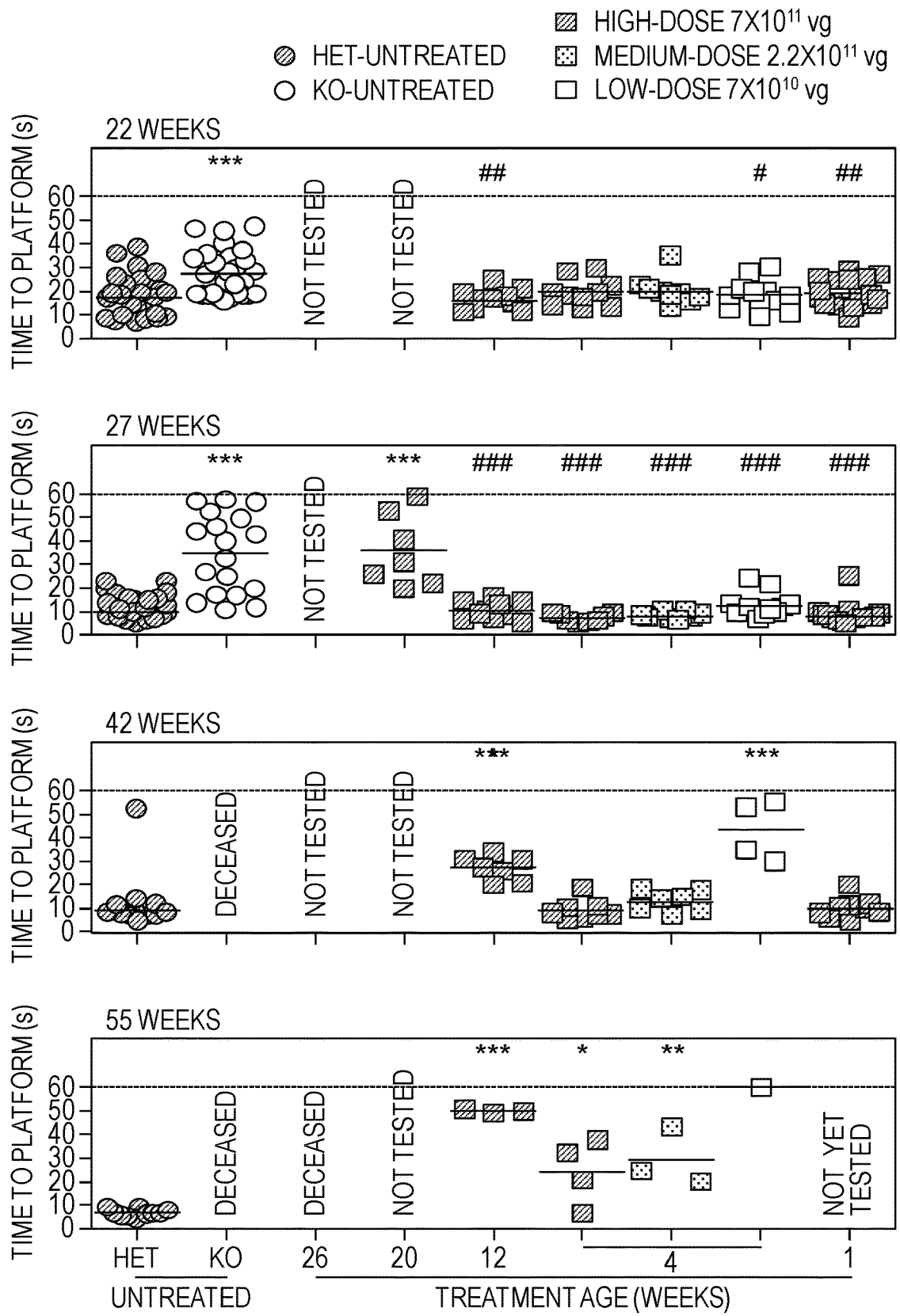
FIGS. 10A-10B show time to find platform in the Morris Water Maze. Each point represents the time to find the platform for a given mouse at the tested age averaged across 2-3 days with 4 trials per day. A. Cohorts whose behavioral testing began at <1 yr of age. A one-way ANOVA with Tukey's post-hoc multiple comparison was used to assess differences in group means as compared to untreated HETs (*) or untreated KOs (#): */#p<0.05, /##p<0.01, */###p<0.001. B. Cohort whose behavioral testing began at >1 yr of age. Differences in group means were determined by the unpaired Student's t test: p<0.01, *p<0.001.
Figure 10B:
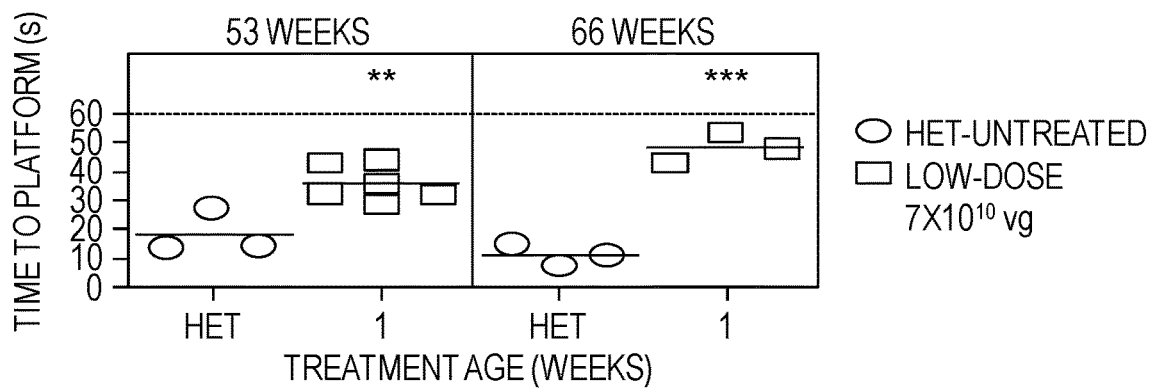
Figure 11B:
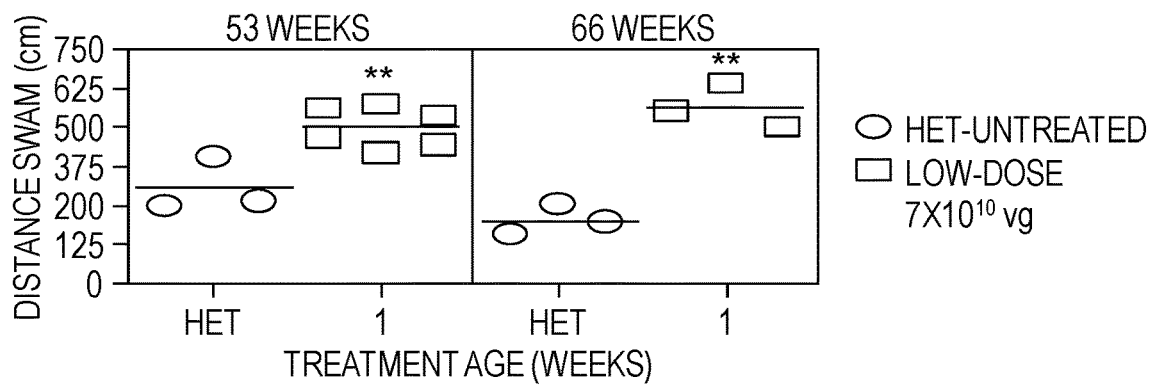
FIGS. 11A-11B show distance swam in the Morris Water Maze. Each point represents the distance swam for a given mouse at the tested age averaged across 2-3 days with 4 trials per day. A. Cohorts whose behavioral testing began at <1 yr of age. A one-way ANOVA with Tukey's post-hoc multiple comparison was used to assess differences in group means as compared to untreated HETs (*) or untreated KOs (#): /##p<0.01, */###p<0.001. B. Cohort whose behavioral testing began at >1 yr of age. Differences in group means were determined by the unpaired Student's t test: **p<0.01.
Figure 11A:
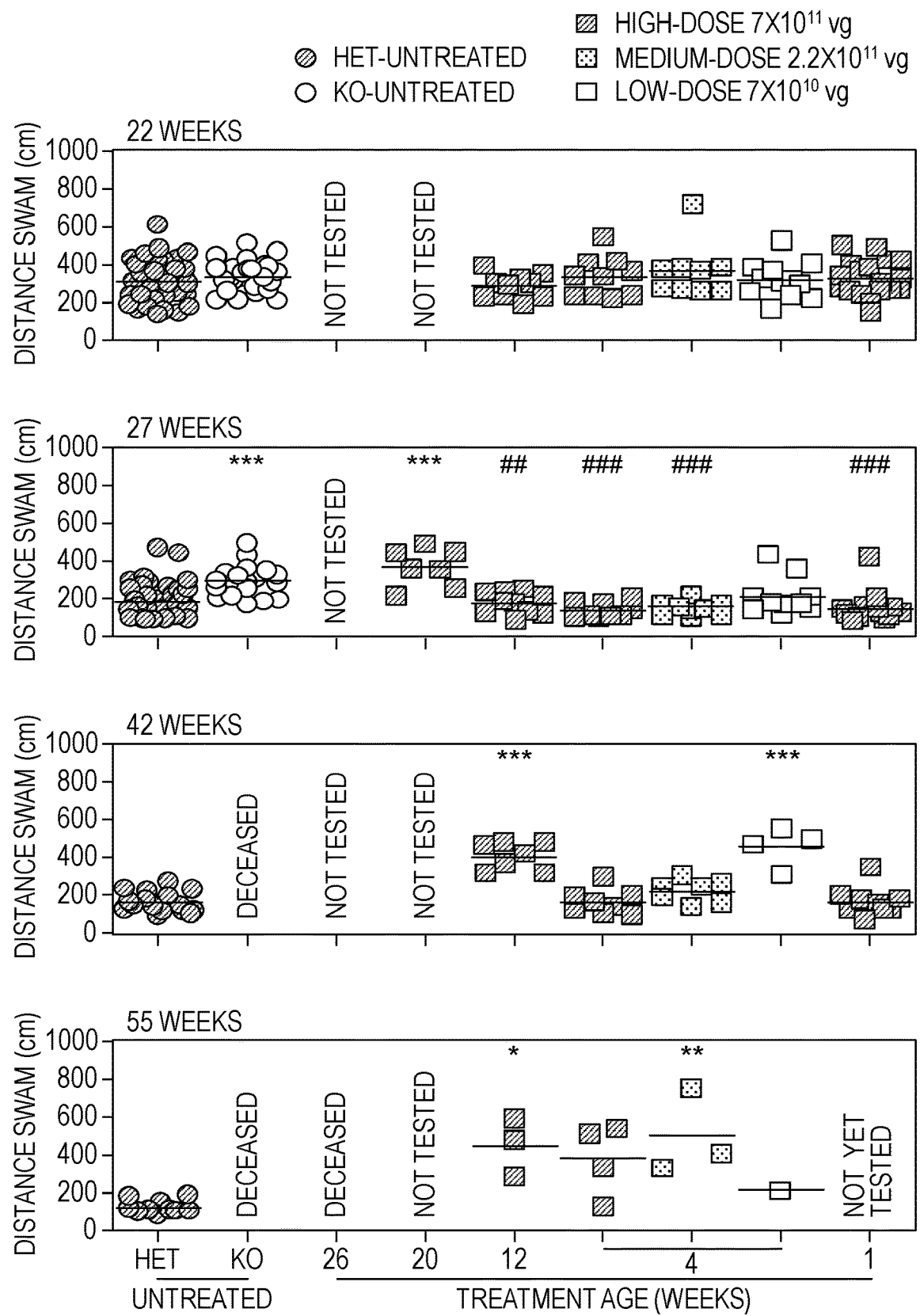

In a test of swimming ability and visual function, mice (heterologous untreated, knockout untreated, knockout treated with low ($7\times10^{10}$ vg), medium ($2.2\times10^{11}$ vg), or high dose ($7\times10^{11}$ vg) at different ages) were placed in a Morris Water Maze consisting of a 122 cm diameter pool filled with 45 cm deep water located in a room with numerous visual cues. Each mouse was given 4 trials per day, across 2-3 days, to swim to an escape platform cued by a patterned cylinder extending above the surface of the water. For each trial, the mouse was placed in the pool at 1 of 4 possible locations (randomly ordered), and then given 60 seconds to find the visible platform. If the mouse found the platform, the trial ended, and the animal was allowed to remain 10 seconds on the platform before the next trial began. If the platform was not found, the mouse was placed on the platform for 10 seconds, and then given the next trial. Tests were carried out at different ages. Swim speed (FIGS. 9A-9B), time to platform (FIGS. 10A-10B), and distance swam (FIGS. 11A-11B) were measured. Treated knockout mice performed better on these tasks than untreated control knockout mice, with earlier intervention at a higher dose providing the greatest benefit.

Figure 12B:
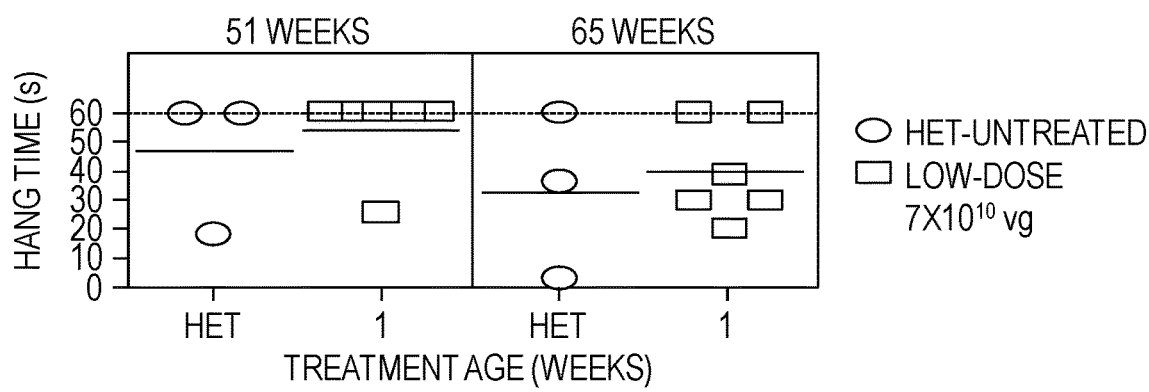
FIGS. 12A-12B show time to fall form inverted wire-hang. Each point represents data for a single mouse at a given testing age. A. Cohorts whose behavioral testing began at <1 yr of age. A one-way ANOVA with Tukey's post-hoc multiple comparison was used to assess differences in group means as compared to untreated HETs (*) or untreated KOs (#):***/###p<0.001. B. Cohort whose behavioral testing began at >1 yr of age. Differences in group means were determined by the unpaired Student's t test.
Figure 13B:
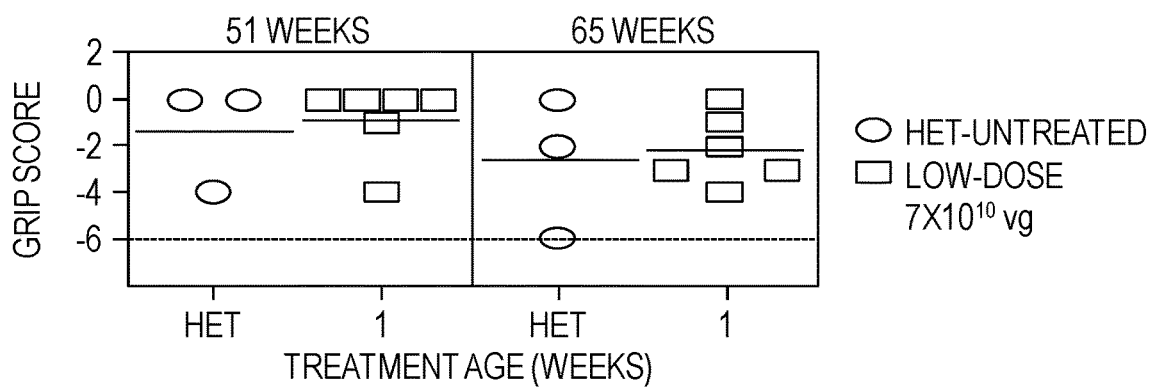
FIGS. 13A-13B show coordination score for inverted wire-hang. Each point represents data for a single mouse at a given testing age. A. Cohorts whose behavioral testing began at <1 yr of age. A one-way ANOVA with Tukey's post-hoc multiple comparison was used to assess differences in group means as compared to untreated HETs (*) or untreated KOs (#):***/###p<0.001. B. Cohort whose behavioral testing began at >1 yr of age. Differences in group means were determined by the unpaired Student's t test.
Figure 12A:
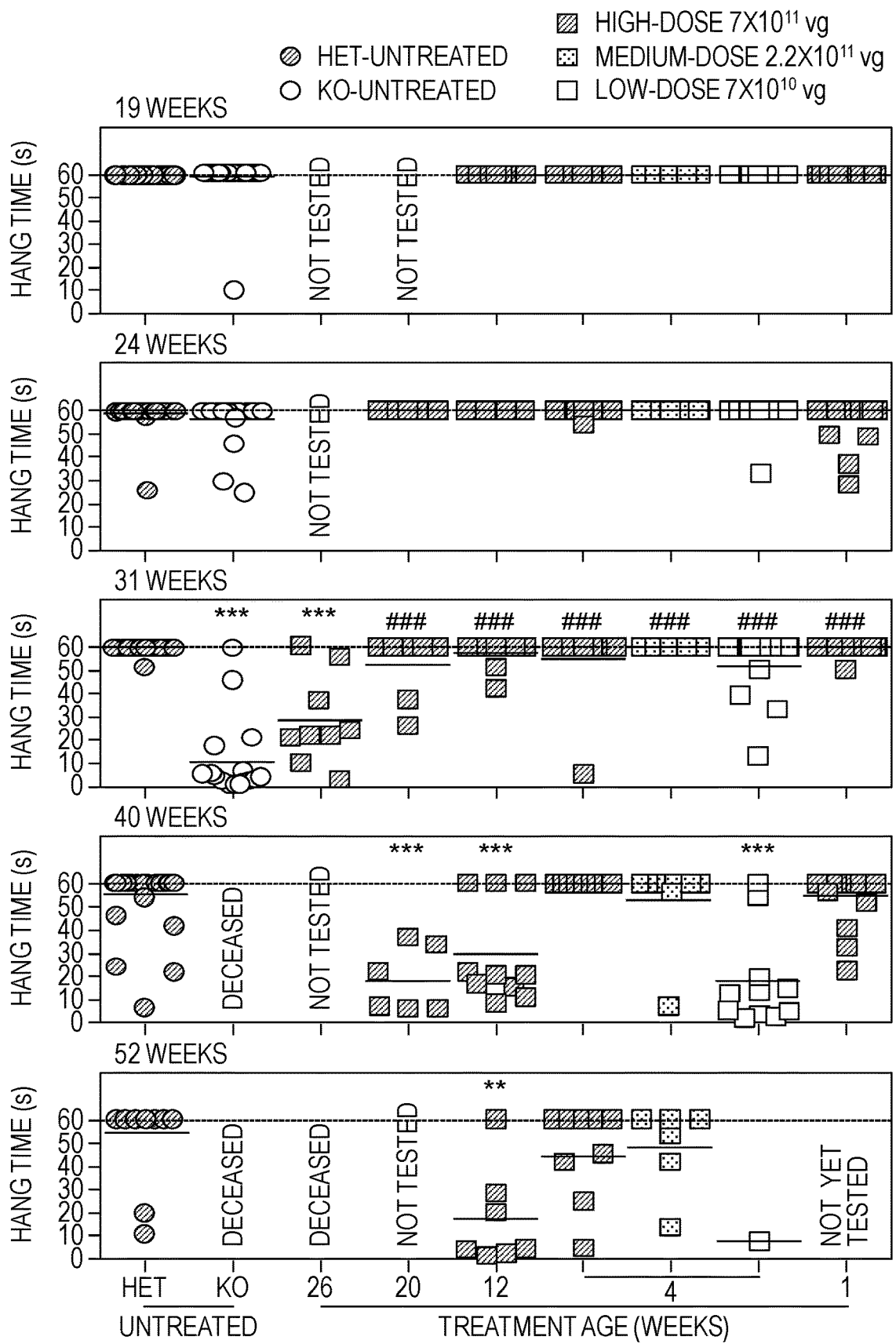
Figure 13A:
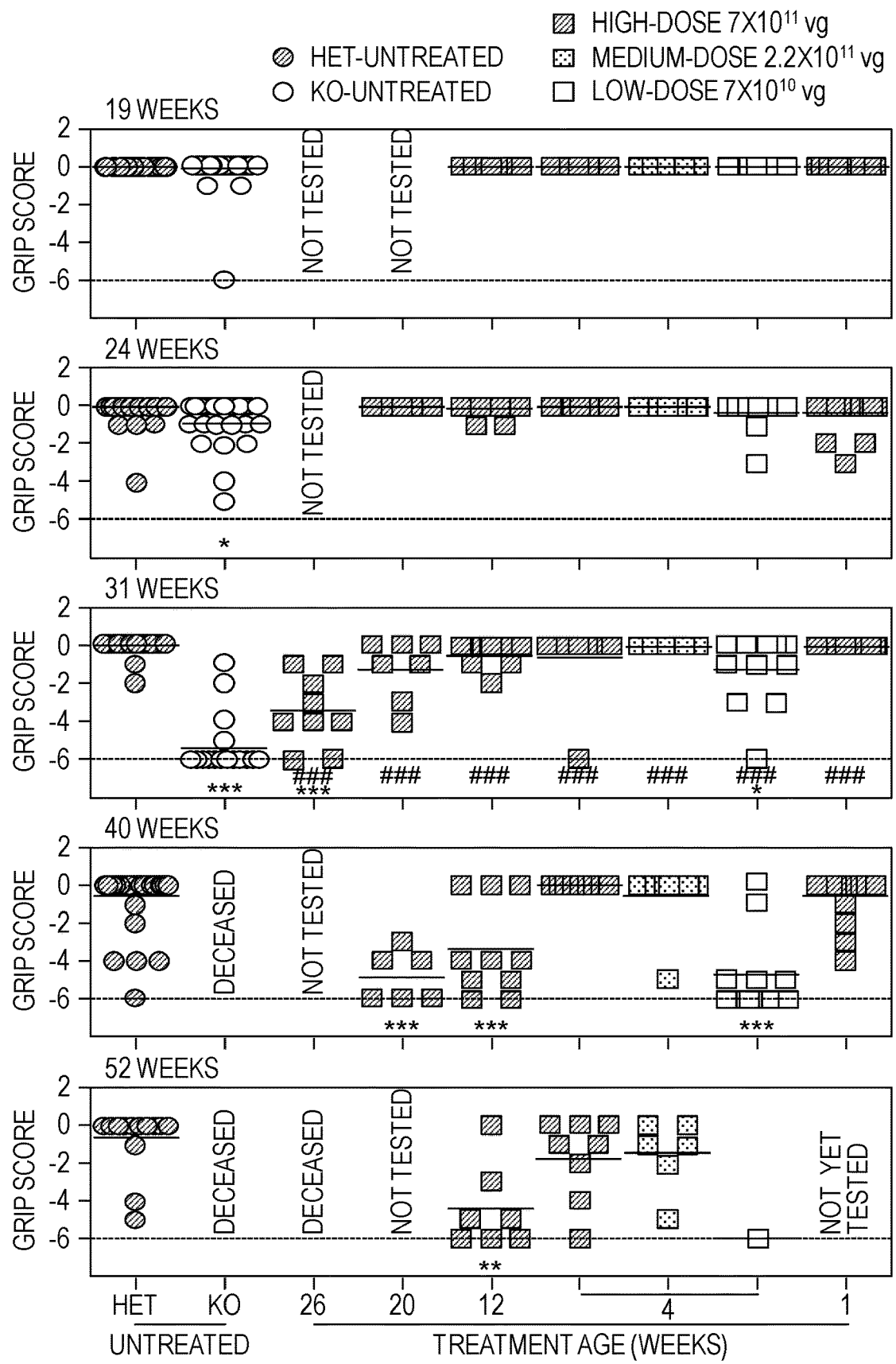

In a test for grip strength, a mouse (heterologous untreated, knockout untreated, knockout treated with low ($7\times10^{10}$ vg), medium ($2.2\times10^{11}$ vg), or high dose ($7\times10^{11}$ vg) at different ages) was placed on a large metal cage lid. The lid was gently shaken to induce the mouse to grip onto the metal grid. The cage top was then flipped over, and latency for the mouse to fall from the lid was recorded. The maximum trial length was 60 seconds. Scoring for the grip was also measured, where −6=mouse falls immediately or within 15 seconds (if mouse falls because of initial unstable placement on lid, a second trial is given); −4=mouse displays awkward gripping ability with either fore- or hind-paws, misses wire with paws, is very unstable on wire (usually falls within 30 seconds); −2=mouse grips wire mostly with limbs, rather than paws., poor turning ability, very unsteady on wire; and 0=mouse exhibits normal, well-coordinated gripping with both fore- and hind-limbs, good turning ability. Tests were carried out at different ages. Time to fall (FIGS. 12A-12B), and coordination score (FIGS. 13A-13B) were measured. Treated knockout mice performed better on these tasks than untreated control knockout mice, with earlier intervention at a higher dose providing the greatest benefit.

Figure 14A:
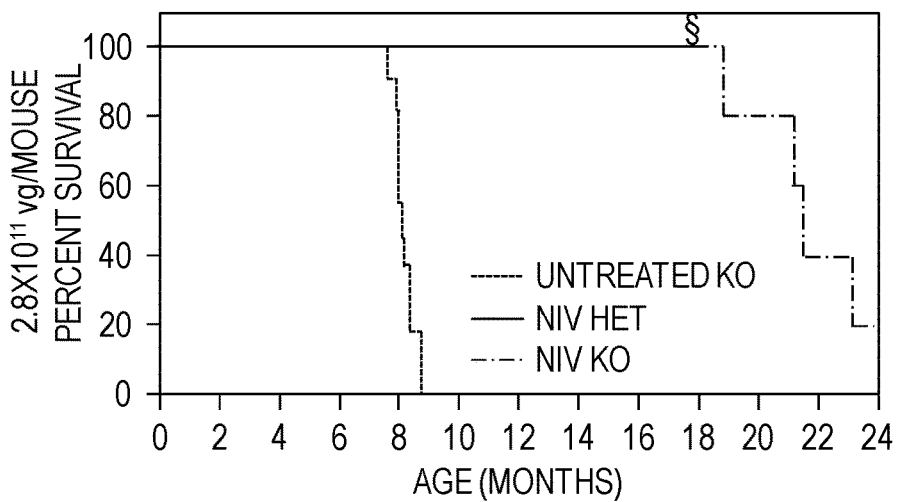
FIGS. 14A-14H show CLN KO and HET mice treated i.v. as neonates have normal lifespans and behavior. All plots are examining mice treated as neonates. A. Kaplan-Meier plot. § indicates that NIV-treated HET animals were healthy, but sacrificed at 18 months for analysis. B. Serum PPT1 activity assay showing NIV-treated HET mice compared to untreated HETs. C. Accelerating Rotarod performance. D. Time to find platform in the Morris Water Maze. E. Swim speed assessment in the Morris Water Maze. F. Distance swam in Morris Water Maze. G. Time to fall from inverted wire-hang. H. Coordination score for inverted wire-hang. Differences between means for treated groups and untreated HETs were determined by the unpaired Student's t test: *p<0.05.
Figure 14B:
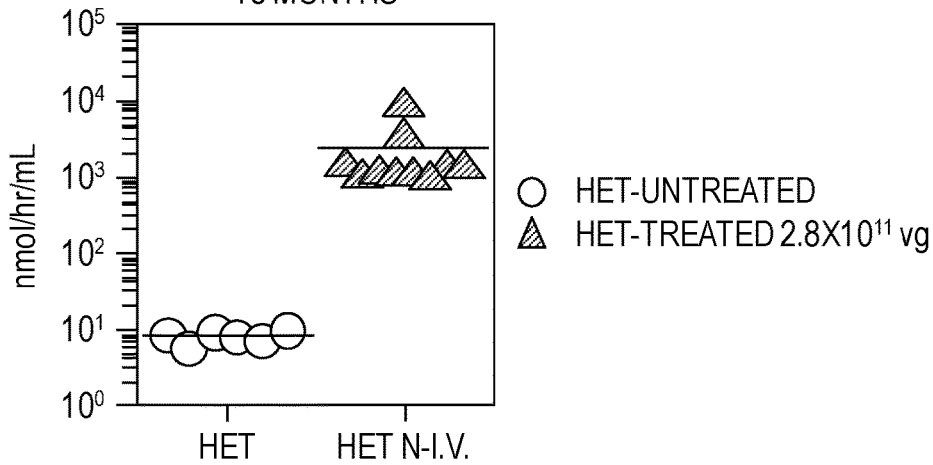
Figure 14C:
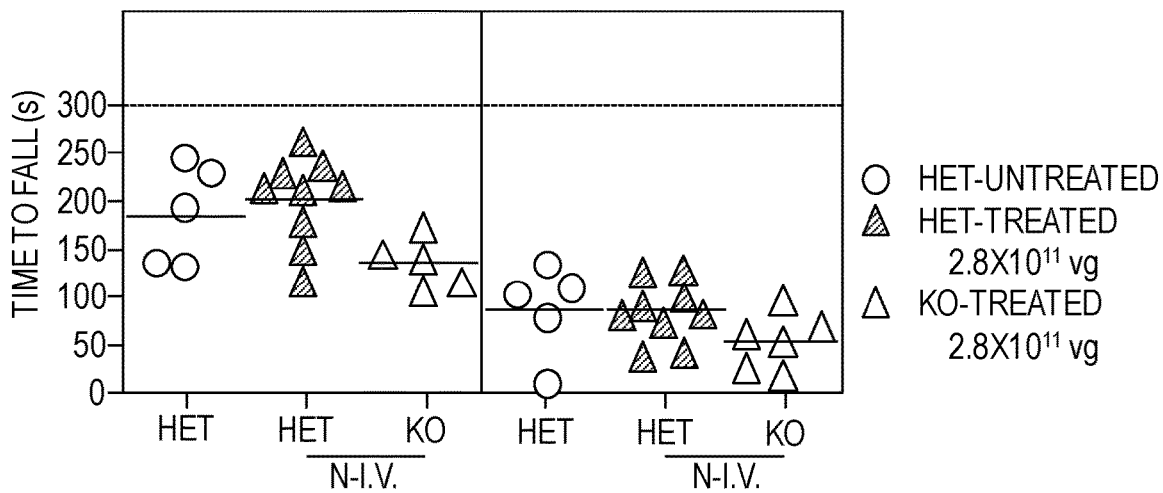
Figure 14D:
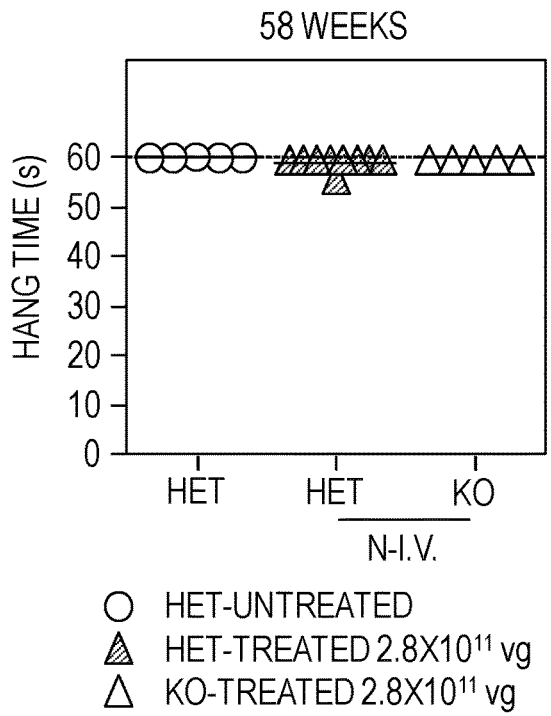
Figure 14E:
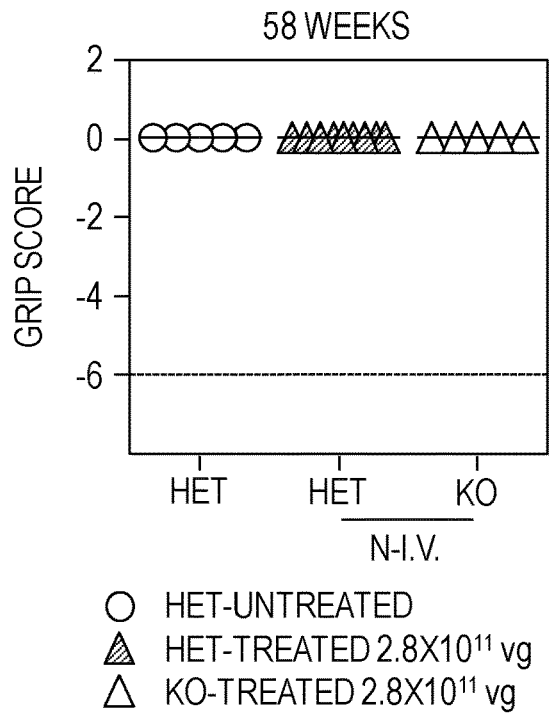
Figure 14F:
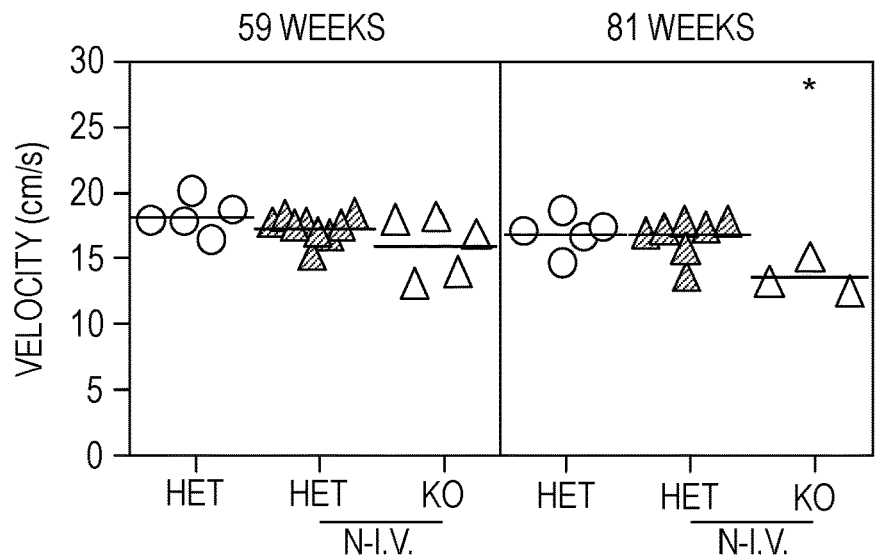
Figure 14G:
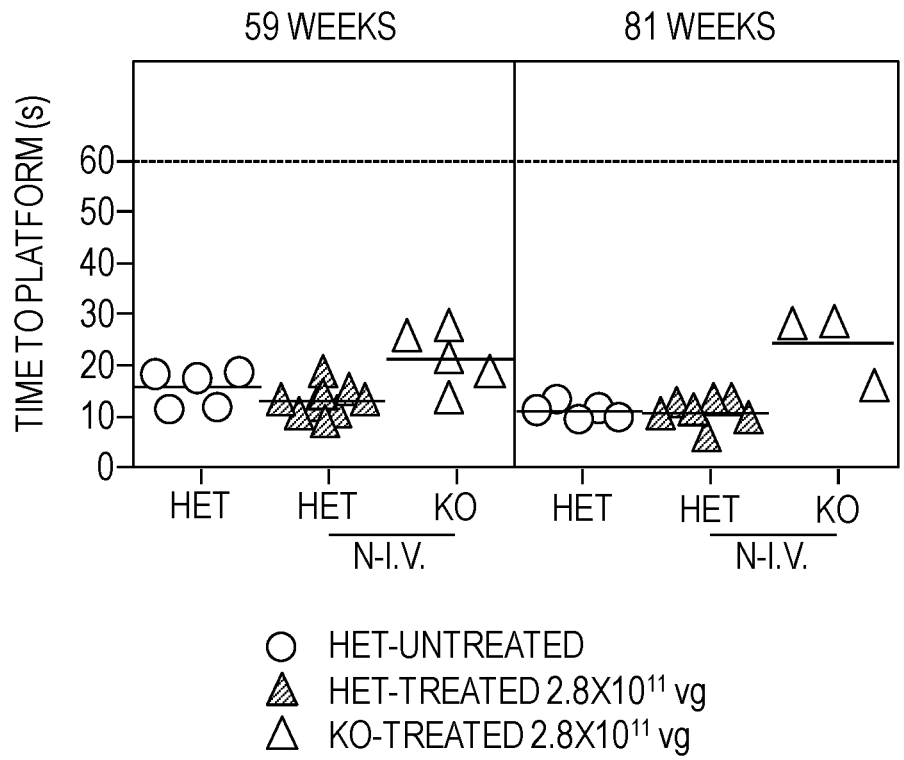

The effect of scAAV9/CLN1 therapy in neonates was tested. Heterologous and CLN1 knockout mice were administered vector ($2.8\times10^{11}$ vg) intravenously as neonates. Survival (FIG. 14A), serum PPT1 levels (FIG. 14B), accelerating rotarod performance (FIG. 14C), time to fall (FIG. 14D), coordination score (FIG. 14E), swimming speed (FIG. 14F), time to platform (FIG. 14G), and distance swam (FIG. 1411) were measured at different ages. The results of these tests show significantly greater function of treated knockout mice compared to untreated control knockout mice, in all areas assessed including prolonged survival. The results do not show any detrimental effects to treated heterozygous mice by any measure evaluated, despite long-term expression of supraphysiological levels of serum PPT1 enzyme activity.

The foregoing is illustrative of the present invention, and is not to be construed as limiting thereof.

The use of the term "or" in the claims is used to mean "and/or" unless explicitly indicated to refer to alternatives only or the alternatives are mutually exclusive, although the disclosure supports a definition that refers to only alternatives and "and/or."

The invention is defined by the following claims, with equivalents of the claims to be included therein.

I claim:

1. A method of expressing a Ceroid-Lipofuscinosis, Neuronal 1 (CLN1) open reading frame in a cell, comprising contacting the cell with a polynucleotide comprising a human CLN1 open reading frame, wherein the human CLN1 open reading frame comprises the nucleotide sequence of SEQ ID NO: 1 or its complement, thereby expressing the CLNI open reading frame in the cell.

2. A method of expressing a CLN1 open reading frame in a subject, comprising delivering to the subject a polynucleotide comprising a human CLN1 open reading frame, wherein the human CLNI open reading frame comprises the nucleotide sequence of SEQ ID NO: 1 or its complement, thereby expressing the CLN1 open reading frame in the subject.

3. A method of treating a disorder associated with aberrant expression of a CLN1 gene or aberrant activity of a CLNI gene product in a subject in need thereof, comprising delivering to the subject a therapeutically effective amount of a polynucleotide comprising a human CLNI open reading frame, wherein the human CLNI open reading frame comprises the nucleotide sequence of SEQ ID NO: 1 or its complement, thereby treating the disorder associated with aberrant expression of the CLNI gene in the subject.

4. The method of claim 3, wherein the disorder associated with expression of the CLN1 gene is infantile, late-infantile, juvenile, or adult-onset neuronal ceroid lipofuscinosis.

5. The method of claim 3, wherein the polynucleotide is delivered to the nervous system of the subject.

6. The method of claim 3, wherein the polynucleotide is delivered by intrathecal, intracerebral, intraventricular, intranasal, intra-aural, intra-ocular, or peri-ocular delivery, or any combination thereof.

7. The method of claim 3, wherein the polynucleotide, expression cassette, vector, and/or transformed cell is delivered intravenously.

8. The method of claim 3, wherein the polynucleotide is operably linked to a promoter, optionally a chicken beta actin promoter.

9. The method of claim 3, wherein the polynucleotide is operably linked to an enhancer, optionally a cytomegalovirus enhancer.

10. The method of claim 3, wherein the polynucleotide is operably linked to an intron, optionally a hybrid/modified mouse parvovirus (MVM) intron.

11. The method of claim 3, wherein the polynucleotide is operably linked to a polyadenylation signal, optionally a bovine growth hormone polyadenylation signal.

12. The method of claim 3, wherein the expression cassette comprises at least one adeno-associated virus (AAV) inverted terminal repeat (ITR).

13. The method of claim 3, wherein the expression cassette is a self-complementary AAV genome.

14. The method of claim 3, wherein the expression cassette comprises an enhancer, a promoter, an intron, a human CLN1 open reading frame, and a polyadenylation site.

15. The method of claim 3, wherein the expression cassette comprises a mutant AAV ITR, a CMV enhancer, a chicken beta actin promoter, a hybrid/modified MVM intron, a human CLN1 open reading frame, a bovine growth hormone polyadenylation site, and a wild-type AAV ITR.

16. The method of claim 15, wherein the expression cassette comprises the nucleotide sequence of SEQ ID NO: 7 or a sequence at least about 90% identical thereto.

17. The method of claim 3, wherein the vector is a viral vector.

18. The method of claim 17, wherein the vector is an AAV vector.

19. The method of claim 18, wherein the AAV vector is an AAV9 vector.

20. The method of claim 19, wherein the AAV vector is a self-complementary AAV9 vector.

21. The method of claim 3, wherein the polynucleotide is delivered intravitreally.

22. The method of claim 3, wherein a disorder associated with aberrant expression of a CLNI gene or aberrant activity of a CLNI gene product is infantile neuronal ceroid lipofuscinosis.

* * * * *

UNITED STATES PATENT AND TRADEMARK OFFICE
CERTIFICATE OF CORRECTION

PATENT NO. : 12,257,322 B2  
APPLICATION NO. : 18/052082  
DATED : March 25, 2025  
INVENTOR(S) : Steven Gray Page 1 of 1

It is certified that error appears in the above-identified patent and that said Letters Patent is hereby corrected as shown below:

In the Specification

Column 2, Line 62: Please correct "MV=neonatal IV;" to read --NIV=neonatal IV;--

Column 27, Line 54: Please correct "$10^3$," to read --$10^{13}$,--

Column 29, Line 12: Please correct "MUDS," to read --MUPS,--

Figure 14H:
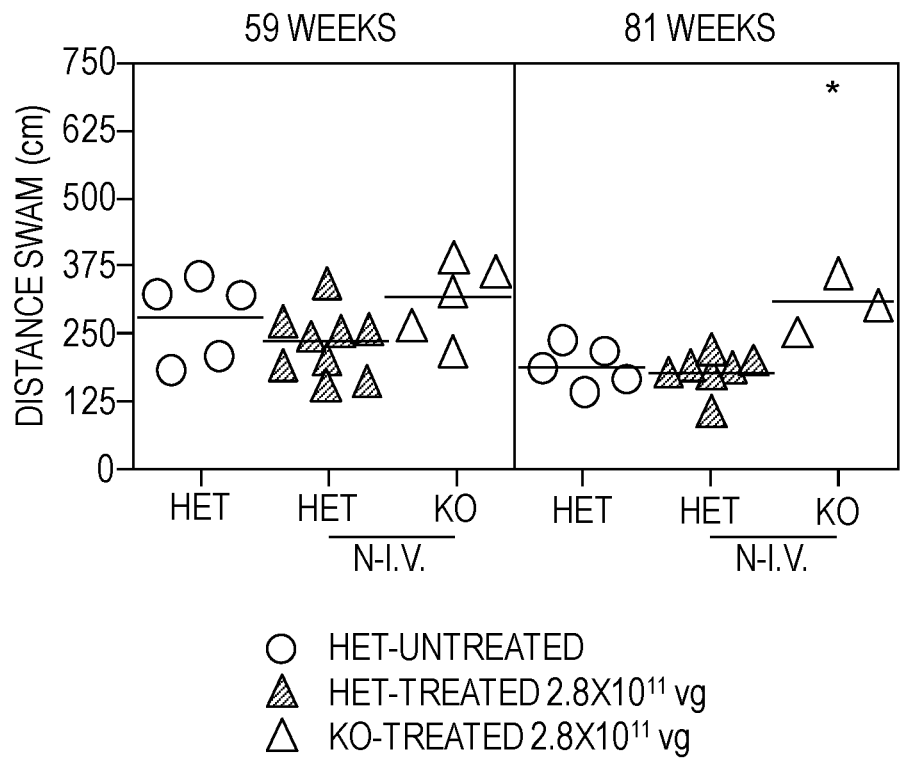

Column 32, Lines 50-51: Please correct "(FIG 1411)" to read --(FIG. 14H)--

In the Claims

Column 35, Line 56, Claim 1: Please correct "CLNI" to read --CLN1--

Column 35, Line 60, Claim 2: Please correct "CLNI" to read --CLN1--

Column 35, Line 65, Claim 3: Please correct "CLNI" to read --CLN1--

Column 36, Line 48, Claim 3: Please correct "CLNI" to read --CLN1--

Column 36, Line 49, Claim 3: Please correct "CLNI" to read --CLN1--

Column 36, Line 52, Claim 3: Please correct "CLNI" to read --CLN1--

Signed and Sealed this  
Ninth Day of December, 2025

John A. Squires  
*Director of the United States Patent and Trademark Office*

SEQUENCE LISTING

```
Sequence total quantity: 7
SEQ ID NO: 1                moltype = DNA   length = 924
FEATURE                     Location/Qualifiers
misc_feature                1..924
                            note = Synthetic human codon-optimized CLN1 open reading
                             frame
source                      1..924
                            mol_type = other DNA
                            organism = synthetic construct
SEQUENCE: 1
atggcttctc cggggtgtct gtggctgctg gcagtggcac tccttccctg gacttgcgcc   60
agccgggctc tgcagcacct cgaccctcca gcccctcttc cactggtgat ttggcacgga  120
atgggtgatt cctgctgtaa tccctgtca atgggagcca tcaagaagat ggtggagaag  180
aagatccctg gaatctacgt gctgtcactg gagattggaa agaccctgat ggaggacgtc  240
gagaactcct tcttcctcaa tgtcaactct caagtgctca ccgtctgcca ggccctgggc  300
aaggacccga agctgcagca ggggtataat gctatgggt tcagccaggg aggacagttc  360
cttcgggctg tggcccaacg ctgccctagc cacccatga tcaacctgat ctcagtgggt  420
ggccagcatc agggcgtgtt cggacttccc cggtgtcccg ggaatcctc tcatatctgc  480
gacttcatcc gcaaaactct caatgcaggc gcttattcaa aggtcgtcca agagaggctg  540
gtgcaagccg agtactggca cgatcccatt aaggaggacg tgtacagaaa tcactcaatc  600
tttctggccg acattaacca ggagagggga attaacgaat catataagaa gaatctcatg  660
gccctcaaaa agttcgtcat ggtgaagttc cttaacgata gcattgtgga cccagtggac  720
agcgaatggt tcggatttta ccgctcaggc caggcaaaag aaaccatccc tctccaagag  780
acttctcttt acacccaaga cagacttggg cttaaggaaa tggataacgc tggtcagctg  840
gtgttcctcg ccaccgaagg tgaccatctg cagctcagcg aagagtggtt ctacgctcat  900
atcatcccgt ttcttggttg ataa                                         924

SEQ ID NO: 2                moltype = DNA   length = 306
FEATURE                     Location/Qualifiers
source                      1..306
                            mol_type = other DNA
                            organism = Gallus gallus
SEQUENCE: 2
tacgtattag tcatcgctat taccatggtc gaggtgagcc ccacgttctg cttcactctc   60
cccatctccc cccctcccc accccaatt ttgtatttat ttatttttta attatttgt   120
gcagcgatgg gggcgggggg ggggggggg cgcgcgccaa gcgggggccgg gcgggcgagg  180
gggcgggcg gggcgaggcg gagaggtgcg gcggcagcca atcagagcgg cgcgctccga  240
aagtttcctt ttatggcgag gcggcggcgg cggcggccct ataaaaagcg aagcgcgcgg  300
cgggcg                                                             306

SEQ ID NO: 3                moltype = DNA   length = 137
FEATURE                     Location/Qualifiers
source                      1..137
                            mol_type = other DNA
                            organism = Gallus gallus
SEQUENCE: 3
ggagtcgctg cgacgctgcc ttcgcccgt gcccgctcc gccgccgcct cgcgccgccc   60
gccccggctc tgactgaccg cgttactccc acaggtgagc gggcgggacg gcccttctcc  120
tccgggctgt aattagc                                                 137

SEQ ID NO: 4                moltype = DNA   length = 256
FEATURE                     Location/Qualifiers
source                      1..256
                            mol_type = other DNA
                            organism = Cytomegalovirus sp.
SEQUENCE: 4
tacataactt acggtaaatg gcccgcctgg ctgaccgccc aacgacccccc gcccattgac   60
gtcaatagta acgccaatag ggactttcca ttgacgtcaa tgggtggagt atttacggta  120
aactgcccac ttggcagtac atcaagtgta tcatatgcca agtacgcccc ctattgacgt  180
caatgacggt aaatggcccg cctggcattg tgcccagtac atgaccttat gggactttcc  240
tacttggcag tacatc                                                  256

SEQ ID NO: 5                moltype = DNA   length = 92
FEATURE                     Location/Qualifiers
misc_feature                1..92
                            note = Synthetic hybrid/modified MVM intron
source                      1..92
                            mol_type = other DNA
                            organism = synthetic construct
SEQUENCE: 5
aagaggtaag ggtttaaggg atggttggtt ggtggggtat taatgtttaa ttacctggag   60
cacctgcctg aaatcacttt ttttcaggtt gg                                92

SEQ ID NO: 6                moltype = DNA   length = 254
FEATURE                     Location/Qualifiers
source                      1..254
                            mol_type = other DNA
                            organism = Bos taurus
```

```
SEQUENCE: 6
ctcgactgtg ccttctagtt gccagccatc tgttgtttgc ccctccccg tgccttcctt      60
gaccctggaa ggtgccactc ccactgtcct ttcctaataa aatgaggaaa ttgcatcgca    120
ttgtctgagt aggtgtcatt ctattctggg gggtggggtg gggcaggaca gcaaggggga    180
ggattgggaa gacaacagca ggcatgctgg ggatgcggtg ggctctatgg cttctgaggc    240
ggaaagaacc agct                                                      254

SEQ ID NO: 7            moltype = DNA   length = 2302
FEATURE                 Location/Qualifiers
misc_feature            1..2302
                        note = Synthetic CLN1 expression cassette
source                  1..2302
                        mol_type = other DNA
                        organism = synthetic construct
SEQUENCE: 7
ctgcgcgctc gctcgctcac tgaggccgcc cgggcaaagc ccgggcgtcg ggcgacctt      60
ggtcgcccgg cctcagtgag cgagcgagcg cgcagagagg gagtgggtt cggtacccgt    120
tacataactt acggtaaatg gcccgcctgg ctgaccgccc aacgacccccc gcccattgac   180
gtcaatagta acgccaatag ggactttcca ttgacgtcaa tgggtggagt atttacggta    240
aactgcccac ttggcagtac atcaagtgta tcatatgcca agtacgcccc ctattgacgt    300
caatgacggt aaatggcccg cctggcattg tgcccagtac atgaccttat gggactttcc    360
tacttggcag tacatctacg tattagtcat cgctattacc atggtcgagg tgagccccac    420
gttctgcttc actctcccca tctcccccccc ctccccaccc ccaatttgt atttatttat    480
tttttaatta ttttgtgcag cgatggggg ggggggggg ggggggcgcg cgccaggcgg      540
ggcggggcgg ggcgaggggc ggggcgggc gaggcggaga ggtgcggcgg cagccaatca    600
gagcggcgcg ctccgaaagt ttccttttat ggcagacggg cggcggcggc ggcccctataa   660
aaagcgaagc gcgcggcggg cgggagtcgc tgcgacgctg ccttcgcccc gtgccccgct    720
ccgccgccgc ctcgcgccgc ccgccccggc tctgactgac cgcgttactc ccacaggtga    780
gcgggcggga cggccctct cctccgggct gtaattagct gagcaagagg taaggggtta    840
agggatggtt ggttggtggg gtattaatgt ttaattacct ggagcacctg cctgaaatca    900
ctttttttca ggttggaccg gtcgccacca tggcttctcc ggggtgtctg tggctgctgg    960
cagtggcact ccttccctgg acttgcgcca gccgggctct gcagcacctc gaccctccag   1020
ccctcttcc actggtgatt tggcacgaaa tgggtgattc ctgctgtaat ccctgtcaa    1080
tgggagccat caagaagatg gtggagaaga agatccctgg aatctacgtg ctgtcactgg   1140
agattggaaa gaccctgatg gaggacgtcg agaactcctt cttcctcaat gtcaactctc   1200
aagtgaccac cgtctgccag gccctggcca aggacccgaa gctgcagcag gggtataatg   1260
ctatgggtt cagccaggga ggacagttcc ttcgggctgt ggcccaacgc tgccctagcc   1320
cacccatgat caacctgatc tcagtgggtg gccagcactga gggcgtgttc ggacttcccc   1380
ggtgtcccgg ggaatcctct catatctgcg acttcatccg caaaactctc aatgcaggcg   1440
cttattcaaa ggtcgtccaa gagaggctgg tgcaagccga gtactggcac gatcccatta   1500
aggaggacgt gtacagaaat cactcaatct ttctggccga cattaaccag gagaggggaa   1560
ttaacgaatc atataagaag aatctcatgg ccctcaaaaa gttcgtcatg gtgaagttcc   1620
ttaacgatag cattgtggac ccagtggaca gcgaatggtt cggattttac cgctcaggcc   1680
aggcaaaaga aaccatccct ctccaagaga cttctcttta cacccaagac agacttgggc   1740
ttaaggaaat ggataacgct ggtcagctgg tgttcctcgc caccgaaggt gaccatctgc   1800
agctcagcga agagtggttc tacgctcata tcatcccgtt tcttggttga taagcggccg   1860
cggggatccc tcgactgtgc cttctagttg ccagccatct gttgtttgcc cctcccccgt   1920
gccttccttg accctggaag gtgccactcc cactgtcctt tcctaataaa atgaggaaat   1980
tgcatcgcat tgtctgagta ggtgtcattc tattctgggg ggtggggtgg ggcaggacag   2040
caaggggag gattgggaag acaacagcag gcatgctggg gatgcggtgg gctctatggc   2100
ttctgaggcg gaaagaacca gctttggacg cgtaggaacc cctagtgatg gagttgccaa   2160
ctccctctct gcgcgctcgc tcgctcactg aggccgggcg accaaaggtc gcccgacgcc   2220
cgggctttgc ccgggcggcc tcagtgagcg agcgagcgcg cagctgcgt aatagcgaag    2280
aggcccgcac cgatcgccct tc                                            2302
```